United States Patent [19]
Reeders et al.

[11] Patent Number: 5,973,120
[45] Date of Patent: Oct. 26, 1999

[54] α-3 CHAIN TYPE IV COLLAGEN POLYPEPTIDES

[75] Inventors: Stephen T. Reeders, Hamden, Conn.; Karen E. Morrison, Cambridge, United Kingdom; Billy G. Hudson, Lenexa, Kans.

[73] Assignees: Yale University, New Haven, Conn.; University of Kansas Medical Center, Kansas City, Kans.

[21] Appl. No.: 08/399,889

[22] Filed: Mar. 7, 1995

Related U.S. Application Data

[62] Division of application No. 07/621,091, Nov. 30, 1990, Pat. No. 5,424,408.

[51] Int. Cl.$^6$ .................................................. C07K 14/47
[52] U.S. Cl. ........................................ 530/356; 536/23.5
[58] Field of Search ............................ 530/356; 536/23.5

[56] References Cited

U.S. PATENT DOCUMENTS

| | | | |
|---|---|---|---|
| 4,394,443 | 7/1983 | Weissman et al. | 435/6 |
| 4,800,159 | 1/1989 | Mullis et al. | 435/172.3 |

OTHER PUBLICATIONS

Butkowski et al, *J. Lab. Clin Med.*, 115, (1990), pp. 365–373 "Characterization of type IV collagen NC1 monomers and Goodpasture antigen in human renal basement membranes".
Saus et al, *The Journal of Biological Chemistry*, 263, (1988), pp. 13374–13380, "Identification of the Goodpasture Antigen as the α2(IV) Chain of Collagen IV".
Morrison et al, *The Journal of Biological Chemistry*, 266, (1991), pp. 34–39, "Use of the Polymerase Chain Reaction to Clone and Sequence a cDNA Encoding the Bovine α2 Chain of Type IV Collagen".
Dion et al, *J. Mol. Biol.*, (1987) 193, pp. 127–143, "COOH–terminal Propeptide of the Major Human Procollagens Structural, Functional and Genetic Comparisons".
Erkki Soini et al, *Clinical Chemistry*, vol. 25, No. 3, 1979 pp. 353–361, "Fluoroimmunoassay: Present Status and Key Problems".
Taina Pihlajaniemi et al, *The Journal of Biological Chemistry*, vol. 265, No. 23, pp. 13758–13766, 1990, "Complete Primary Structure of the Triple–helical Region and the Carboxyl–terminal Domain of a New Type IV Collagen Chain, α5(IV)".
Feinberg et al, *Analytical Biochemistry*, 132, pp. 6–13 (1983), "A Technique for Radiolabeling DNA Restriction Endonuclease Fragments to High Specifc Activity".
McCoy et al, *Kidney International*, vol. (1982), pp. 642–652, "Absence of nephritogenic GBM antigen(s) in some patients with hereditary nephritis".
Brinker et al, *Proc. Natl. Acad. Sci. USA*, vol. 82, pp. 3649–3653, Jun. 1985, Biochemistry, "Restricted homology between α1 type IV and other procollagen chains".
U.K. Laemmli, *Nature*, vol. 227, (1970) "Cleavage of Structural Proteins during the Assembly of the Head of Bacteriophage T4" pp. 680–685.
Piotr Chomzczynski et al, *Analytical Biochemistry*, 162, pp. 156–159, "Single–Step Method of RNA Isolation by Acid Guanidinium Thiocyanate–Phenol–Chloroform Extraction".
Timpl et al, *J. Biochem.*, 120, pp. 203–211, (1981), "A Network Model for the Organization of Type IV Collagen Molecules in Basement Membranes".
Martin et al, *Advances in Protein Chemistry*, vol. 39, (1988) pp. 1–51, "Basement Membrane Proteins: Molecular Structure and Function".
Timpl, *Eur. J. Biochem.* 180, 487–502 (1989), "Structure and Biological activity of basement membrane proteins".
Hostikka et al, *The Journal of Biological Chemistry*, vol. 263, No. 36, (1988), pp. 19488–19493, "The Complete Primary Structure of the α2 Chain of Human Type IV Collagen and Comparison with the α1(IV) Chain".
Muthukumaran et al, *The Journal of Biological Chemistry*, vol. 264, No. 11 (1989) pp. 6310–6317, "The Complete Primary Structure for the α1–Chain of Mouse Collagen IV".
Saus et al, *The Journal of Biological Chemistry*, vol. 264, (1989), pp. 6318–6324, "The Complete Primary Structure of Mouse α2(IV) Collagen".
Blumberg et al, *The Journal of Biological Chemistry*, vol. 263, No. 34, (1988), pp. 18328–18337, "Drosophila Basement Membrane procollagen α1(IV)".
Butkowski et al, *The Journal of Biological Chemistry*, vol. 260, No. 6, (1985), pp. 3739–3747, "Properties of the Globular Domain of Type IV Collagen and Its Relationship to the Goodpasture Antigen".
Wieslander et al, *The Journal of Biological Chemsitry*, vol. 260, No. 260, No. 14, (1985), pp. 8564–8570, "Physical and Immunochemical Studies of the Globular Domain of Type IV Collagen".
Butkowski et al, *The Journal of Biological Chemistry*, vol. 262, No. 16 (1987) pp. 7874–7877, "Localization of the Goodpasture Epitope to a Novel Chain of Basement Membrane Collagen".
Hudson et al, *Laboratory Investigation*, vol. 61, No. 3 pp. 256–269, (1989), "Biology of Disease Goodpasture Syndrome: Molecular Architecture and Function of Basement Membrane Antigen".

(List continued on next page.)

*Primary Examiner*—Charles L. Patterson, Jr.
*Attorney, Agent, or Firm*—McDonnel Boehnen Hulbert & Berghoff

[57] ABSTRACT

An isolated and substantially pure polynucleotide encoding 238 amino acids of the carboxy terminal end of the triple helical domain and all 233 amino acids of the carboxy terminal noncollageneous domain of the bovine α3 chain of type IV collagen. An isolated and substantially pure polynucleotide encoding 218 amino acids of the carboxy terminal noncollagenous domain of the human α3 chain of type IV collagen. Such polynucleotides are useful to express large amounts of proteins in vectors and such expressed proteins are useful to detect Goodpasture antibodies in blood and to remove Goodpasture antibodies from the bloodstream of patients suffering from Goodpasture syndrome.

3 Claims, 7 Drawing Sheets

OTHER PUBLICATIONS

Kleppel et al, *The Journal of Biological Chemistry*, vol. 261, No. 35, (1986), pp. 16547–16552, "Antibody Specificity of Human Glomerular Basement Membrane Type IV Collagen NC1 Subunits".

Jeraj et al, *American Journal of Kidney Diseases*, vol. 11, No. 6, (1983), "Absence of Goodpasture's Antigen in Male Patients With Familial Nephritis".

Kashtan et al, *J. Clin. Invest.*, vol. 78, (1986), pp. 1035–1044, Nephritogenic Antigen Determinants in Epidermal and Renal Basement Membranes of Kindreds with Alport–type Familial Nephritis.

Jenis et al, *Clinical Nephrology*, vol. 15, No. 3 (1981) pp. 111–114, "Variability of anti–GBM binding in hereditary nephritis".

Olson et al, *The Journal of Pediatrics*, vol. 96, (1980) pp. 697–699, "Diagnosis of Hereditary nephritis by failure of glomeruli to bind anti–glomerular basement membrane antibodies".

Savage et al, *Kidney International*, vol. 30, (1986) pp. 107–112, "The Goodpasture antigen in Alport's syndrome: Studies with a monoclonal antibody".

Hostikka et al, *Proc. Natl. Acad. Sci. USA*, vol. 87, (1990) pp. 1606–1610, "Identification of a distinct type IV collagen α chain with restricted kidney distributin and assignment of its gene to the locus of X chromosome–linked Alport syndrome".

Myers et al, *Am. J. Hum. Genet.*, 46:1024–1033, (1990), pp. 1024–1033, "Molecular Cloning of α5(IV) Collagen and Assignment of the Gene to the Region of the X Chromosome Containing the Alport Syndrome Locus".

Atkin et al, *Am. J. Hum. Genet.*, 42:249–255, (1988), pp. 249–255, "Mapping of Alport Syndrome to the Long Arm of the X Chromosome".

Brunner et al, *Kidney International*, vol. 34, (1988), pp. 507–510. "Localization of the gene for X–linked Alport's syndrome".

Flinter et al, *Genomics*, vol. 4, pp. 335–338 (1989), "Localization of the Gene for Classic Alport Syndrome".

Barker et al, *Science*, vol. 248, pp. 1224–1227, (1990), "Identification of Mutations in the COL4A5 Collagen Gene in Alport Syndrome".

Pihlajaniemi et al, *The Journal of Biological Chemistry*, vol. 260, No. 12, (1985), pp. 7681–7687, "cDNA Clones Coding for the Pro–α1 (IV) Chain of Human Type IV Procollagen Reveal an Unusual Homologyof Amino Acid Sequences in Two Halves of the Carboxyl–terminal Domain".

Gunwar et al, *The Journal of Biological Chemistry*, vol. 265, No. 10, (1990), pp. 5446–5469, "Glomerular Basement Membrane".

Grunfeld, *Kidney International*, vol. 27, (1985), pp. 83–92, "The clinical spectrum of hereditary nephritis".

Hinglais, et al, *Laboratory Investigation*, vol. 27, (1972) No. 5, pp. 473–487, "Characteristic Ultrastructural Lesion of the Glomerular Basement Membrane in Progressive Hereditary Nephritis (Alport's Syndrome)".

Yoshikawa et al, *J. Pathology*, vol. 135, (1981), 199–209, "The Glomerular Basal Lamina in Hereditary Nephritis".

Henry et al, *Clinical Chemistry*, vol. 22, No. 7, 1976, p. 1232, "Debate on the Procedure of Rao et al for Creatine Kinase".

S. Szpiro–Tapia et al, *Hum. Genet.*, (1988) vol. 81, pp. 85–87, "Linkage studies in X–linked Alport's syndrome".

Kleppel et al, *J. Clin. Invest.*, vol. 80, (1987), pp. 263–265, "Alport Familial Nephritis Absence of 28 Kilodalton Non–Collagenous Monomers of Type IV Collagen in Glomerular Basement Membrane".

Soininen et al, *Febs Letters*, vol. 225, No. 1,2, pp. 188–194, (1987), "Complete primary structure of the α1–chain of human basement membrane (type IV) collagen".

M2

M₂ = GOOD PASTURE ANTIGEN
α3 NC1 MONOMER.

| | | |
|---|---|---|
| F1: | 5' – AAGCCNGGNGA(C,T)ACAGG – 3' | (5) |
| F2: | 5' – AAGCCNGGNGA(C,T)ACCGG – 3' | (5) |
| F3: | 5' – AAGCCNGGNGA(C,T)ACGGG – 3' | (5) |
| F4: | 5' – AAGCCNGGNGA(C,T)ACTGG – 3' | (5) |
| R1: | 5' – TA(A,G)TG(T,C)CTNGT(A,G)AANACAAA – 3' | (28) |
| R2: | 5' – TA(A,G)TG(T,C)CTNGT(A,G)AANACGAAA – 3' | (28) |
| R3: | 5' – TA(A,G)TGNCGNGT(A,G)AANACAAA – 3' | (28) |
| R4: | 5' – TA(A,G)TGNCGNGT(A,G)AANACGAA – 3' | (28) |
| | | |
| FA: | 5' – GCNGGNCGNGTNATGCG – 3' | (14) |
| FB: | 5' – GCNGGNCGNGTNATGAG – 3' | (14) |
| FC: | 5' – GTNTT(C,T)ACNAG(A,G)CA(C,T)TATC – 3' | (22) |
| FD: | 5' – CCAGG(A,C)GA(C,T)AC(A,C,T)GGNCC(A,C,T)CCAG – 3' | (6) |
| RA: | 5' – CAGGAAGGGCAT(G,T)GTGCTGAA – 3' | [165] |
| RB: | 5' – GG(G,C)GCCTCACACACAG(A,C)ACA – 3' | [317] |
| RC: | 5' – TTGCAG(A,T)ACAGGAAGGGCAT – 3' | [173] |
| RD: | 5' – TTGCAG(A,T)ACAGGAAGGG – 3' | [173] |
| | | |
| F9*: | 5' – CCCGATGGGTTGCCAGGATCCAT – 3' | [-42] |
| R9*: | 5' – TGACTATGCCTGGTCACAAG – 3' | [37] |

5,973,120

SEQUENCE LISTING

```
<160> NUMBER OF SEQ ID NOS: 25

<210> SEQ ID NO 1
<211> LENGTH: 1416
<212> TYPE: DNA
<213> ORGANISM: Calf
<220> FEATURE:
<221> NAME/KEY: CDS
<222> LOCATION: (1)..(1416)

<400> SEQUENCE: 1
```

-continued

| | |
|---|---|
| ggc ctc cct ggc agg aaa ggg cca gtg gga gat gct ggg cct cca ggc<br>Gly Leu Pro Gly Arg Lys Gly Pro Val Gly Asp Ala Gly Pro Pro Gly<br>1                       5                    10                  15 | 48 |
| cag ctt ggc gtg aca gga cct caa ggg gca cca ggc ttt cct ggt gta<br>Gln Leu Gly Val Thr Gly Pro Gln Gly Ala Pro Gly Phe Pro Gly Val<br>                   20                    25                    30 | 96 |
| acc atc cct ggc cag aaa gga gat cga ggt cca cct ggc tcc aga gga<br>Thr Ile Pro Gly Gln Lys Gly Asp Arg Gly Pro Pro Gly Ser Arg Gly<br>          35                    40                    45 | 144 |
| aac cca ggc atg cct ggt cct cct gga cct cca ggg agt cct gta gaa<br>Asn Pro Gly Met Pro Gly Pro Pro Gly Pro Pro Gly Ser Pro Val Glu<br>50                      55                    60 | 192 |
| ggc ata aaa gga gac aag ggg ttg atg gga gag cct ggc caa aga ggt<br>Gly Ile Lys Gly Asp Lys Gly Leu Met Gly Glu Pro Gly Gln Arg Gly<br>65                      70                    75                  80 | 240 |
| cca cct gga gct ata gga gac atg ggg tca cca ggt cat ccg gga gca<br>Pro Pro Gly Ala Ile Gly Asp Met Gly Ser Pro Gly His Pro Gly Ala<br>                    85                    90                    95 | 288 |
| cca ggt gtc ccc ggt cag cca ggg gcc aga ggt gat cct gga ttc tat<br>Pro Gly Val Pro Gly Gln Pro Gly Ala Arg Gly Asp Pro Gly Phe Tyr<br>                  100                 105                110 | 336 |
| gga ttt cca ggc atg aaa ggg aag aag ggt aat tca gga ttt cca gga<br>Gly Phe Pro Gly Met Lys Gly Lys Lys Gly Asn Ser Gly Phe Pro Gly<br>                  115                 120                125 | 384 |
| cca cct gga cct cca ggg caa agt gga cca aaa gga cca cct gga gta<br>Pro Pro Gly Pro Pro Gly Gln Ser Gly Pro Lys Gly Pro Pro Gly Val<br>130                   135                 140 | 432 |
| cgt gga gag cct ggc aca gtg aag atc atc tcc ctt cca gga agc cca<br>Arg Gly Glu Pro Gly Thr Val Lys Ile Ile Ser Leu Pro Gly Ser Pro<br>145                   150                 155                160 | 480 |
| ggc cca cct ggt tca gct gga gaa cca ggg atg caa gga gaa ccc ggg<br>Gly Pro Pro Gly Ser Ala Gly Glu Pro Gly Met Gln Gly Glu Pro Gly<br>                  165                 170                175 | 528 |
| ccc cca gga cca cca gga gat cca gga ccc tgt ggg cca aaa ggt aaa<br>Pro Pro Gly Pro Pro Gly Asp Pro Gly Pro Cys Gly Pro Lys Gly Lys<br>                  180                 185                190 | 576 |
| cca ggg gag gat ggt cca cca gga act cct gga cca act gga gaa aaa<br>Pro Gly Glu Asp Gly Pro Pro Gly Thr Pro Gly Pro Thr Gly Glu Lys<br>                  195                 200                205 | 624 |
| ggc aac aaa ggt tgt aaa gga gag caa gga cca cct gga tcc gat ggc<br>Gly Asn Lys Gly Cys Lys Gly Glu Gln Gly Pro Pro Gly Ser Asp Gly<br>210                 215                 220 | 672 |
| ctg cca ggc ttg aag ggg aaa cct gga gac act gga cca cct gca gca<br>Leu Pro Gly Leu Lys Gly Lys Pro Gly Asp Thr Gly Pro Pro Ala Ala<br>225                 230                 235                240 | 720 |
| ggg gca gtg atg agg ggc ttt gtc ttt acc cgg cac agc cag acc aca<br>Gly Ala Val Met Arg Gly Phe Val Phe Thr Arg His Ser Gln Thr Thr<br>                  245                 250                255 | 768 |
| gca att ccc tcc tgt cca gaa ggg aca gag ccg ctc tat agt ggg ttt<br>Ala Ile Pro Ser Cys Pro Glu Gly Thr Glu Pro Leu Tyr Ser Gly Phe<br>                  260                 265                270 | 816 |
| tct ctt ctc ttt gta caa gga aat gaa caa gcc cat gga cag gac ctg<br>Ser Leu Leu Phe Val Gln Gly Asn Glu Gln Ala His Gly Gln Asp Leu<br>                  275                 280                285 | 864 |
| gga aca ctt ggc agc tgc ctg cag cga ttt acc aca atg cca ttc tta<br>Gly Thr Leu Gly Ser Cys Leu Gln Arg Phe Thr Thr Met Pro Phe Leu<br>                  290                 295                300 | 912 |
| ttc tgc aat atc aac gat gta tgt aat ttt gca tct cga aac gat tat<br>Phe Cys Asn Ile Asn Asp Val Cys Asn Phe Ala Ser Arg Asn Asp Tyr<br>305                 310                 315                320 | 960 |

| | | | | | | | | | | | | | | | | |
|---|---|---|---|---|---|---|---|---|---|---|---|---|---|---|---|---|
| tca | tac | tgg | ctg | tca | aca | cca | gct | atg | ata | cca | atg | gac | atg | gct | cca | 1008 |
| Ser | Tyr | Trp | Leu | Ser | Thr | Pro | Ala | Met | Ile | Pro | Met | Asp | Met | Ala | Pro | |
| | | | 325 | | | | | 330 | | | | | 335 | | | |

| | | | | | | | | | | | | | | | | |
|---|---|---|---|---|---|---|---|---|---|---|---|---|---|---|---|---|
| att | act | ggc | agg | gcc | ctg | gag | cct | tat | att | agc | aga | tgt | aca | gtc | tgt | 1056 |
| Ile | Thr | Gly | Arg | Ala | Leu | Glu | Pro | Tyr | Ile | Ser | Arg | Cys | Thr | Val | Cys | |
| | | | 340 | | | | | 345 | | | | | 350 | | | |

| | | | | | | | | | | | | | | | | |
|---|---|---|---|---|---|---|---|---|---|---|---|---|---|---|---|---|
| gaa | ggt | cct | gca | att | gcc | ata | gct | gtt | cac | agc | caa | acc | act | gat | atc | 1104 |
| Glu | Gly | Pro | Ala | Ile | Ala | Ile | Ala | Val | His | Ser | Gln | Thr | Thr | Asp | Ile | |
| | | | 355 | | | | | 360 | | | | | 365 | | | |

| | | | | | | | | | | | | | | | | |
|---|---|---|---|---|---|---|---|---|---|---|---|---|---|---|---|---|
| ccc | ccc | tgt | cct | gct | ggc | tgg | att | tct | ctc | tgg | aaa | ggc | ttt | tct | ttc | 1152 |
| Pro | Pro | Cys | Pro | Ala | Gly | Trp | Ile | Ser | Leu | Trp | Lys | Gly | Phe | Ser | Phe | |
| | | 370 | | | | | 375 | | | | | 380 | | | | |

| | | | | | | | | | | | | | | | | |
|---|---|---|---|---|---|---|---|---|---|---|---|---|---|---|---|---|
| atc | atg | ttc | aca | agt | gct | ggt | tcg | gag | ggt | gct | ggg | caa | gca | ctc | gca | 1200 |
| Ile | Met | Phe | Thr | Ser | Ala | Gly | Ser | Glu | Gly | Ala | Gly | Gln | Ala | Leu | Ala | |
| 385 | | | | | 390 | | | | | 395 | | | | | 400 | |

| | | | | | | | | | | | | | | | | |
|---|---|---|---|---|---|---|---|---|---|---|---|---|---|---|---|---|
| tcc | ccc | ggc | tcc | tgc | ctg | gaa | gaa | ttc | cga | gcc | agt | cca | ttt | ata | gaa | 1248 |
| Ser | Pro | Gly | Ser | Cys | Leu | Glu | Glu | Phe | Arg | Ala | Ser | Pro | Phe | Ile | Glu | |
| | | | | 405 | | | | | 410 | | | | | 415 | | |

| | | | | | | | | | | | | | | | | |
|---|---|---|---|---|---|---|---|---|---|---|---|---|---|---|---|---|
| tgt | cac | gga | aga | gga | aca | tgt | aac | tac | tat | tca | aac | tcc | tac | agt | ttc | 1296 |
| Cys | His | Gly | Arg | Gly | Thr | Cys | Asn | Tyr | Tyr | Ser | Asn | Ser | Tyr | Ser | Phe | |
| | | | 420 | | | | | 425 | | | | | 430 | | | |

| | | | | | | | | | | | | | | | | |
|---|---|---|---|---|---|---|---|---|---|---|---|---|---|---|---|---|
| tgg | ttg | gct | tca | tta | gac | ccc | aaa | aga | atg | ttc | aga | aaa | cct | att | cca | 1344 |
| Trp | Leu | Ala | Ser | Leu | Asp | Pro | Lys | Arg | Met | Phe | Arg | Lys | Pro | Ile | Pro | |
| | | | 435 | | | | | 440 | | | | | 445 | | | |

| | | | | | | | | | | | | | | | | |
|---|---|---|---|---|---|---|---|---|---|---|---|---|---|---|---|---|
| tca | act | gtg | aaa | gct | ggg | gag | tta | gaa | aac | ata | ata | agt | cgc | tgt | caa | 1392 |
| Ser | Thr | Val | Lys | Ala | Gly | Glu | Leu | Glu | Asn | Ile | Ile | Ser | Arg | Cys | Gln | |
| | | | 450 | | | | | 455 | | | | | 460 | | | |

| | | | | | | | |
|---|---|---|---|---|---|---|---|
| gtg | tgc | atg | aag | atg | aga | cca | tga | 1416 |
| Val | Cys | Met | Lys | Met | Arg | Pro | | |
| 465 | | | | 470 | | | | |

<210> SEQ ID NO 2
<211> LENGTH: 657
<212> TYPE: DNA
<213> ORGANISM: Human
<220> FEATURE:
<221> NAME/KEY: CDS
<222> LOCATION: (1)..(657)

<400> SEQUENCE: 2

| | | | | | | | | | | | | | | | | |
|---|---|---|---|---|---|---|---|---|---|---|---|---|---|---|---|---|
| caa | acc | aca | gca | att | cct | tca | tgt | cca | gag | ggg | aca | gtg | cca | ctc | tac | 48 |
| Gln | Thr | Thr | Ala | Ile | Pro | Ser | Cys | Pro | Glu | Gly | Thr | Val | Pro | Leu | Tyr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| agt | ggg | ttt | tct | ttt | ctt | ttt | gta | caa | gga | aat | caa | cga | gcc | cac | gga | 96 |
| Ser | Gly | Phe | Ser | Phe | Leu | Phe | Val | Gln | Gly | Asn | Gln | Arg | Ala | His | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| caa | gac | ctt | gga | act | ctt | ggc | agc | tgc | ctg | cag | cga | ttt | acc | aca | atg | 144 |
| Gln | Asp | Leu | Gly | Thr | Leu | Gly | Ser | Cys | Leu | Gln | Arg | Phe | Thr | Thr | Met | |
| | | | 35 | | | | | 40 | | | | | 45 | | | |

| | | | | | | | | | | | | | | | | |
|---|---|---|---|---|---|---|---|---|---|---|---|---|---|---|---|---|
| cca | ttc | tta | ttc | tgc | aat | gtc | aat | gat | gta | tgt | aat | ttt | gca | tct | cga | 192 |
| Pro | Phe | Leu | Phe | Cys | Asn | Val | Asn | Asp | Val | Cys | Asn | Phe | Ala | Ser | Arg | |
| | | 50 | | | | | 55 | | | | | 60 | | | | |

| | | | | | | | | | | | | | | | | |
|---|---|---|---|---|---|---|---|---|---|---|---|---|---|---|---|---|
| aat | gat | tat | tca | tac | tgg | ctg | tca | aca | cca | gct | ctg | atg | cca | atg | aac | 240 |
| Asn | Asp | Tyr | Ser | Tyr | Trp | Leu | Ser | Thr | Pro | Ala | Leu | Met | Pro | Met | Asn | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| atg | gct | ccc | att | act | ggc | aga | gcc | ctt | gag | cct | tat | ata | agc | aga | tgc | 288 |
| Met | Ala | Pro | Ile | Thr | Gly | Arg | Ala | Leu | Glu | Pro | Tyr | Ile | Ser | Arg | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| act | gtt | tgt | gaa | ggt | cct | gcg | atc | gcc | ata | gcc | gtt | cac | agc | caa | acc | 336 |
| Thr | Val | Cys | Glu | Gly | Pro | Ala | Ile | Ala | Ile | Ala | Val | His | Ser | Gln | Thr | |
| | | | | 100 | | | | | 105 | | | | | 110 | | |

-continued

| | | | | | | | | | | | | | | | |
|---|---|---|---|---|---|---|---|---|---|---|---|---|---|---|---|
| act | gac | att | cct | cca | tgt | cct | cac | ggc | tgg | att | tct | ctc | tgg | aaa | gga | 384
| Thr | Asp | Ile | Pro | Pro | Cys | Pro | His | Gly | Trp | Ile | Ser | Leu | Trp | Lys | Gly |
| | 115 | | | | | 120 | | | | | 125 | | | | |

| ttt | tca | ttc | atc | atg | ttc | aca | agt | gca | ggt | tct | gag | ggc | gcc | ggg | caa | 432
| Phe | Ser | Phe | Ile | Met | Phe | Thr | Ser | Ala | Gly | Ser | Glu | Gly | Ala | Gly | Gln |
| 130 | | | | | 135 | | | | | 140 | | | | | |

| gca | ctg | gcc | tcc | ccc | ggc | tcc | tgc | ctg | gaa | gaa | ttc | cga | gcc | agc | cca | 480
| Ala | Leu | Ala | Ser | Pro | Gly | Ser | Cys | Leu | Glu | Glu | Phe | Arg | Ala | Ser | Pro |
| 145 | | | | | 150 | | | | | 155 | | | | | 160 |

| ttt | cta | gaa | tgt | cat | gga | aga | gga | acg | tgc | aac | tac | tat | tca | aat | tcc | 528
| Phe | Leu | Glu | Cys | His | Gly | Arg | Gly | Thr | Cys | Asn | Tyr | Tyr | Ser | Asn | Ser |
| | | | | 165 | | | | | 170 | | | | | 175 | |

| tac | agt | ttc | tgg | ctg | gct | tca | tta | aac | cca | gaa | aga | atg | ttc | aga | aag | 576
| Tyr | Ser | Phe | Trp | Leu | Ala | Ser | Leu | Asn | Pro | Glu | Arg | Met | Phe | Arg | Lys |
| | | | 180 | | | | | 185 | | | | | 190 | | |

| cct | att | cca | tca | act | gtg | aaa | gct | ggg | gaa | tta | gaa | aaa | ata | ata | agt | 624
| Pro | Ile | Pro | Ser | Thr | Val | Lys | Ala | Gly | Glu | Leu | Glu | Lys | Ile | Ile | Ser |
| | | 195 | | | | | 200 | | | | | 205 | | | |

| cgc | tgt | cag | gtg | tgc | atg | aag | aaa | aga | cac | tga | | | | | | 657
| Arg | Cys | Gln | Val | Cys | Met | Lys | Lys | Arg | His | | | | | | |
| | 210 | | | | | 215 | | | | | | | | | |

<210> SEQ ID NO 3
<211> LENGTH: 12
<212> TYPE: PRT
<213> ORGANISM: Human

<400> SEQUENCE: 3

Ile Ser Arg Cys Gln Val Cys Met Lys Lys Arg His
 1               5                  10

<210> SEQ ID NO 4
<211> LENGTH: 17
<212> TYPE: DNA
<213> ORGANISM: Human
<220> FEATURE:
<221> NAME/KEY: n at position 6 and 9 can be a, t, c, or g
<222> LOCATION: 6 and 9
<223> OTHER INFORMATION: DNA

<400> SEQUENCE: 4
aagccnggng ayacagg                                                    17

<210> SEQ ID NO 5
<211> LENGTH: 17
<212> TYPE: DNA
<213> ORGANISM: Human
<220> FEATURE:
<221> NAME/KEY: n at position 6 and 9 can be a, t, c, or g
<222> LOCATION: 6 and 9
<223> OTHER INFORMATION: DNA

<400> SEQUENCE: 5
aagccnggng ayaccgg                                                    17

<210> SEQ ID NO 6
<211> LENGTH: 17
<212> TYPE: DNA
<213> ORGANISM: Human
<220> FEATURE:
<221> NAME/KEY: n at position 6 and 9 can be a, t, c, or g
<222> LOCATION: 6 and 9
<223> OTHER INFORMATION: DNA

```
<400> SEQUENCE: 6
aagccnggng ayacggg                                                17

<210> SEQ ID NO 7
<211> LENGTH: 17
<212> TYPE: DNA
<213> ORGANISM: Human
<220> FEATURE:
<221> NAME/KEY: n at position 6 and 9 can be a, t, c, or g
<222> LOCATION: 6 and 9
<223> OTHER INFORMATION: DNA

<400> SEQUENCE: 7
aagccnggng ayactgg                                                17

<210> SEQ ID NO 8
<211> LENGTH: 20
<212> TYPE: DNA
<213> ORGANISM: Human
<220> FEATURE:
<221> NAME/KEY: n at position 9 and 15 can be a, t, c, or g
<222> LOCATION: 9 and 15
<223> OTHER INFORMATION: DNA

<400> SEQUENCE: 8
tartgyctng traanacaaa                                             20

<210> SEQ ID NO 9
<211> LENGTH: 20
<212> TYPE: DNA
<213> ORGANISM: Human
<220> FEATURE:
<221> NAME/KEY: n at position 9 and 15 can be a, t, c, or g
<222> LOCATION: 9 and 15
<223> OTHER INFORMATION: DNA

<400> SEQUENCE: 9
tartgyctng traanacgaa                                             20

<210> SEQ ID NO 10
<211> LENGTH: 20
<212> TYPE: DNA
<213> ORGANISM: Human
<220> FEATURE:
<221> NAME/KEY: n at position 6, 9 and 15 can be a, t, c, or g
<222> LOCATION: 6, 9 and 15
<223> OTHER INFORMATION: DNA

<400> SEQUENCE: 10
tartgncgng traanacaaa                                             20

<210> SEQ ID NO 11
<211> LENGTH: 20
<212> TYPE: DNA
<213> ORGANISM: Human
<220> FEATURE:
<221> NAME/KEY: n at position 6, 9 and 15 can be a, t, c, or g
<222> LOCATION: 6, 9 and 15
<223> OTHER INFORMATION: DNA

<400> SEQUENCE: 11
tartgncgng traanacgaa                                             20

<210> SEQ ID NO 12
<211> LENGTH: 17
<212> TYPE: DNA
<213> ORGANISM: Human
<220> FEATURE:
```

<221> NAME/KEY: n at position 3, 6, 9 and 12 can be a, t, c, or g
<222> LOCATION: 3, 6, 9 and 12
<223> OTHER INFORMATION: DNA

<400> SEQUENCE: 12
gcnggncgng tnatgcg                                                        17

<210> SEQ ID NO 13
<211> LENGTH: 17
<212> TYPE: DNA
<213> ORGANISM: Human
<220> FEATURE:
<221> NAME/KEY: n at position 3, 6, 9 and 12 can be a, t, c, or g
<222> LOCATION: 3, 6, 9 and 12
<223> OTHER INFORMATION: DNA

<400> SEQUENCE: 13
gcnggncgng tnatgag                                                        17

<210> SEQ ID NO 14
<211> LENGTH: 19
<212> TYPE: DNA
<213> ORGANISM: Human
<220> FEATURE:
<221> NAME/KEY: n at position 3 and 9 can be a, t, c, or g
<222> LOCATION: 3 and 9
<223> OTHER INFORMATION: DNA

<400> SEQUENCE: 14
gtnttyacna grcaytatc                                                      19

<210> SEQ ID NO 15
<211> LENGTH: 22
<212> TYPE: DNA
<213> ORGANISM: Human
<220> FEATURE:
<221> NAME/KEY: n at position 15 can be a, t, c, or g
<222> LOCATION: 15
<223> OTHER INFORMATION: DNA

<400> SEQUENCE: 15
ccaggmgaya chggncchcc ag                                                  22

<210> SEQ ID NO 16
<211> LENGTH: 21
<212> TYPE: DNA
<213> ORGANISM: Human

<400> SEQUENCE: 16
caggaagggc atkgtgctga a                                                   21

<210> SEQ ID NO 17
<211> LENGTH: 20
<212> TYPE: DNA
<213> ORGANISM: Human

<400> SEQUENCE: 17
ggsgcctcac acacagmaca                                                     20

<210> SEQ ID NO 18
<211> LENGTH: 20
<212> TYPE: DNA
<213> ORGANISM: Human

```
<400> SEQUENCE: 18
ttgcagwaca ggaagggcat                                          20

<210> SEQ ID NO 19
<211> LENGTH: 17
<212> TYPE: DNA
<213> ORGANISM: Human

<400> SEQUENCE: 19
ttgcagwaca ggaaggg                                             17

<210> SEQ ID NO 20
<211> LENGTH: 23
<212> TYPE: DNA
<213> ORGANISM: Human

<400> SEQUENCE: 20
cccgatgggt tgccaggatc cat                                      23

<210> SEQ ID NO 21
<211> LENGTH: 20
<212> TYPE: DNA
<213> ORGANISM: Human

<400> SEQUENCE: 21
tgactatgcc tggtcacaag                                          20

<210> SEQ ID NO 22
<211> LENGTH: 6
<212> TYPE: PRT
<213> ORGANISM: Human

<400> SEQUENCE: 22

Lys Pro Gly Asp Thr Gly
  1               5

<210> SEQ ID NO 23
<211> LENGTH: 7
<212> TYPE: PRT
<213> ORGANISM: Human

<400> SEQUENCE: 23

Tyr His Arg Phe Ala Val Phe
  1               5

<210> SEQ ID NO 24
<211> LENGTH: 471
<212> TYPE: PRT
<213> ORGANISM: Calf

<400> SEQUENCE: 24

Gly Leu Pro Gly Arg Lys Gly Pro Val Gly Asp Ala Gly Pro Pro Gly
  1               5                  10                  15

Gln Leu Gly Val Thr Gly Pro Gln Gly Ala Pro Gly Phe Pro Gly Val
                 20                  25                  30

Thr Ile Pro Gly Gln Lys Gly Asp Arg Gly Pro Pro Gly Ser Arg Gly
             35                  40                  45

Asn Pro Gly Met Pro Gly Pro Pro Gly Pro Pro Gly Ser Pro Val Glu
         50                  55                  60

Gly Ile Lys Gly Asp Lys Gly Leu Met Gly Glu Pro Gly Gln Arg Gly
 65                  70                  75                  80
```

-continued

Pro Pro Gly Ala Ile Gly Asp Met Gly Ser Pro Gly His Pro Gly Ala
                    85                  90                  95

Pro Gly Val Pro Gly Gln Pro Gly Ala Arg Gly Asp Pro Gly Phe Tyr
            100                 105                 110

Gly Phe Pro Gly Met Lys Gly Lys Gly Asn Ser Gly Phe Pro Gly
        115                 120                 125

Pro Pro Gly Pro Pro Gly Gln Ser Gly Pro Lys Gly Pro Pro Gly Val
130                 135                 140

Arg Gly Glu Pro Gly Thr Val Lys Ile Ile Ser Leu Pro Gly Ser Pro
145                 150                 155                 160

Gly Pro Pro Gly Ser Ala Gly Glu Pro Gly Met Gln Gly Glu Pro Gly
                165                 170                 175

Pro Pro Gly Pro Pro Gly Asp Pro Gly Pro Cys Gly Pro Lys Gly Lys
                180                 185                 190

Pro Gly Glu Asp Gly Pro Pro Gly Thr Pro Gly Pro Thr Gly Glu Lys
            195                 200                 205

Gly Asn Lys Gly Cys Lys Gly Glu Gln Gly Pro Pro Gly Ser Asp Gly
        210                 215                 220

Leu Pro Gly Leu Lys Gly Lys Pro Gly Asp Thr Gly Pro Pro Ala Ala
225                 230                 235                 240

Gly Ala Val Met Arg Gly Phe Val Phe Thr Arg His Ser Gln Thr Thr
                245                 250                 255

Ala Ile Pro Ser Cys Pro Glu Gly Thr Glu Pro Leu Tyr Ser Gly Phe
                260                 265                 270

Ser Leu Leu Phe Val Gln Gly Asn Glu Gln Ala His Gly Gln Asp Leu
            275                 280                 285

Gly Thr Leu Gly Ser Cys Leu Gln Arg Phe Thr Thr Met Pro Phe Leu
290                 295                 300

Phe Cys Asn Ile Asn Asp Val Cys Asn Phe Ala Ser Arg Asn Asp Tyr
305                 310                 315                 320

Ser Tyr Trp Leu Ser Thr Pro Ala Met Ile Pro Met Asp Met Ala Pro
                325                 330                 335

Ile Thr Gly Arg Ala Leu Glu Pro Tyr Ile Ser Arg Cys Thr Val Cys
            340                 345                 350

Glu Gly Pro Ala Ile Ala Ile Ala Val His Ser Gln Thr Thr Asp Ile
            355                 360                 365

Pro Pro Cys Pro Ala Gly Trp Ile Ser Leu Trp Lys Gly Phe Ser Phe
            370                 375                 380

Ile Met Phe Thr Ser Ala Gly Ser Glu Gly Ala Gly Gln Ala Leu Ala
385                 390                 395                 400

Ser Pro Gly Ser Cys Leu Glu Glu Phe Arg Ala Ser Pro Phe Ile Glu
            405                 410                 415

Cys His Gly Arg Gly Thr Cys Asn Tyr Tyr Ser Asn Ser Tyr Ser Phe
            420                 425                 430

Trp Leu Ala Ser Leu Asp Pro Lys Arg Met Phe Arg Lys Pro Ile Pro
            435                 440                 445

Ser Thr Val Lys Ala Gly Glu Leu Glu Asn Ile Ile Ser Arg Cys Gln
            450                 455                 460

Val Cys Met Lys Met Arg Pro
465                 470

<210> SEQ ID NO 25
<211> LENGTH: 218

```
<212> TYPE: PRT
<213> ORGANISM: Human

<400> SEQUENCE: 25

Gln Thr Thr Ala Ile Pro Ser Cys Pro Glu Gly Thr Val Pro Leu Tyr
  1               5                  10                  15

Ser Gly Phe Ser Phe Leu Phe Val Gln Gly Asn Gln Arg Ala His Gly
             20                  25                  30

Gln Asp Leu Gly Thr Leu Gly Ser Cys Leu Gln Arg Phe Thr Thr Met
         35                  40                  45

Pro Phe Leu Phe Cys Asn Val Asn Asp Val Cys Asn Phe Ala Ser Arg
     50                  55                  60

Asn Asp Tyr Ser Tyr Trp Leu Ser Thr Pro Ala Leu Met Pro Met Asn
 65                  70                  75                  80

Met Ala Pro Ile Thr Gly Arg Ala Leu Glu Pro Tyr Ile Ser Arg Cys
                 85                  90                  95

Thr Val Cys Glu Gly Pro Ala Ile Ala Ile Ala Val His Ser Gln Thr
                100                 105                 110

Thr Asp Ile Pro Pro Cys Pro His Gly Trp Ile Ser Leu Trp Lys Gly
            115                 120                 125

Phe Ser Phe Ile Met Phe Thr Ser Ala Gly Ser Glu Gly Ala Gly Gln
    130                 135                 140

Ala Leu Ala Ser Pro Gly Ser Cys Leu Glu Glu Phe Arg Ala Ser Pro
145                 150                 155                 160

Phe Leu Glu Cys His Gly Arg Gly Thr Cys Asn Tyr Tyr Ser Asn Ser
                165                 170                 175

Tyr Ser Phe Trp Leu Ala Ser Leu Asn Pro Glu Arg Met Phe Arg Lys
            180                 185                 190

Pro Ile Pro Ser Thr Val Lys Ala Gly Glu Leu Glu Lys Ile Ile Ser
        195                 200                 205

Arg Cys Gln Val Cys Met Lys Lys Arg His
210                 215
```

α-3 CHAIN TYPE IV COLLAGEN POLYPEPTIDES

This is a division of application Ser. No. 07/621.091 filed Nov. 30, 1990, now U.S. Pat. No. 5,424,408

This invention was made with United States government support under Grants DK40703 and DK 18381 from the National Institute of Health. The United States government has certain rights in this invention.

BACKGROUND OF THE INVENTION

FIELD OF THE INVENTION

The present invention concerns alpha3 chain type IV bovine and human polynucleotides and peptides expressed by such polynucleotides which are useful in detecting Goodpasture antibodies and treating Goodpasture syndrome.

BACKGROUND INFORMATION

The major structural component of mammalian basement membranes, type IV collagen, is composed of a number of distinct polypeptide chains (Timpl et al. 1981; Martin et at 1988; Timpl 1989). The most abundant species, α1(IV) and α2(IV) have been extensively characterized in man and mouse and an α type chain from Drosophila also been identified (Soininen et al. 1987; Blumberg et al. 1988; Hostikka and Tryggvason 1988; Saus et al. 1989; Muthukumaran et al. 1989). Characteristics of these collagens include a highly conserved carboxy-terminal noncollagenous (NC1) domain of ~229 residues, a shorter aminoterminal globular domain (7S domain) and a triple helical collagenous domain, in which interruptions occur in the Gly-Xaa-Xaa-Yaa repeat motif, giving a degree of flexibility to the triple helix. Within the membrane matrix the individual collagen chains exist as heterotrimer, which form a supra-molecular structure via interactions between the 7S domains of 4 molecules and the NCI domains of 2 heterotrimers (Timpl et at 1981).

Bacterial collagenase digestion releases the NCI domains from the other components of basement membrane as hexamers, comprised of the 3 NC1 domains from each of 2 interacting collagen heterotrimers. The NCI domains can be further separated on the basis of molecular weight by denaturing polyacrylamide gel electrophoresis. This results in a number of separate monomeric and dimeric subunits (Mr=24,500–28,300 and 40,000–50,7000 respectively), including several which are distinct from the α1(IV) and α2(IV) chains (Butkowski et al. 1985; Wieslander et al. 1985). The monomeric subunits that result from collagenase digestion of human glomerular basement membrane (GBM) have been termed M24, M26, M28+++ and M28+, while the equivalent subunits of bovine basement membranes have been termed M1a, M1b, M2* and M3 (Kleppel et al. 1986; Butkowski et al. 1987). M24 (or M1a) and M26 (or M1b) are the NC1 domains of the α1(IV) and α2(IV) chains. M28+++ (or M2*) and M28+ (or M3) are the NCI domains of 2 novel collagen chains termed α3(V) and α4(V). Short segments of the junction between the collagenous and NCI domains of human and bovine α3(IV) and α4(IV) peptides have been sequenced, confirming that they have a type IV collagen structure (Saus et at 1988; Butkowski et al. 1990).

The α3(IV) chain and the α4(IV) chain are of particular interest as such chains have been implicated in the pathogenesis of Goodpasture syndrome and Alport-type familial nephritis, clinical syndromes that affect GBM and cause functional kidney impairment (Hudson et al. 1989). Goodpasture syndrome is an autoimmune disorder characterized by glomerulonephritis, lung hemorrhage and anti-GBM antibody formation (GlassQck et al. 1986). The nephritis and lung damage are mediated by these anti-GBM antibodies which are primarily targeted at the NC1 domain (M28+++) of α3(IV) (Butkowski et at 1985; Wieslander et al. 1985; Kleppel al.1986). Alport syndrome is an inheritable disorder, characterized by glomerulonephritis, sensorineural hearing loss and various abnormalities of the lens of the eye (Grunfeld, 1985). Ultrastructural GBM abnormalities frequently observed in the syndrome include thinning, diffuse splitting and multilamination of the lamina dense (Hinglais et al. 1972; Yoshikawa et al. 1981). Several investigators have reported that the GBM of some individuals with Alport syndrome does not react in vitro with Goodpasture antibodies nor with a monoclonal antibody that recognizes a Goodpasture epitope, suggesting that there is an abnormality of the α3(IV) chain in these patients (Olsen et at 1980; Jenis et al. 1981; Jeraj et al. 1983; Kashtan et al. 1986; Savage et at 1986; Kleppel et al. 1987).

Recently a gene encoding another novel human type IV collagen chain, COL4A5, was cloned, on the basis of homology with the α1(IV) and α2(IV) chains (Hostikka et al. 1990; Myers et al. 1990). The existence of such a chain had not been expected from biochemical or immunological studies of GBM (glomerular basement molecular), and yet antibodies raised to a peptide fragment synthesized from the predicted amino acid sequence of α5(IV) localized this chain to the GBM (Hostikka et at 1990). COL4A5 maps to Xq22, a region known from genetic linkage studies to contain a locus for Alport Syndrome (Atkin et al. 1988; Brunner et al. 1988; Flinter al. 1988). Further, COL4A5 has been shown to be mutated in 3 of 18 large kindreds with the disease (Barker et al. 1990).

SUMMARY OF THE INVENTION

The present invention concerns an isolated and substantially pure polynucleotide encoding 238 consecutive amino acids from the carboxy terminal end of the triple helical domain and all 233 amino acids of the carboxy terminal noncollageneous domain of the bovine α3 chain of type IV collagen and a nucleotide sequence of said polynucleotide. The invention also directed to a deduced amino acid sequence of the bovine α3 chain of type IV collagen (SEQ ID NO.:24).

The present invention also relates to an isolated and substantially pure polynucleotide encoding 218 consecutive amino acids of the carboxy terminal noncollagenous domain of the human α3 chain of type IV collagen and a nucleotide sequence of said polynucleotide. The invention also directed to a deduced amino acid sequence of the human α3 chain of the type IV collagen (SEQ ID NO.:25).

The above described polynucleotides can be used to express large amounts of proteins in vectors. Such proteins can be used to detect Goodpasture antibodies from the bloodstream of patients suffering from Goodpasture syndrome.

The present invention also concerns a peptide having no more than 218 amino acids of the human α3 chain of type IV collagen comprising the following amino acid sequence:
ISRCQVCMKKRH (Iso Ser Arg Cys Gln Val Cys Met Lys Lys Arg His) (SEQ ID NO:3).

The invention also relates to 6 to all 12 consecutive amino acids of the sequence ISRCQVCMKKRH (SEQ ID NO:3).

The invention also relates to a method for detecting Goodpasture antibodies from a bodily fluid or tissue from a patient, for example, a human, comprising contacting a bodily fluid or tissue from the patient, for example, a human, for example, contacting blood or a liquid fraction thereof, e.g. serum or plasma, with a peptide having no more than 218 amino acids of the human α3 chain of type IV collagen comprising the following amino acid sequence: ISRCQVC-MKKRH (SEQ ID NO:3), whereby if Goodpasture antibodies are present a product will form of the antibodies and peptide and detecting for the presence of Goodpasture antibodies by, for example, by labelling the peptide, e.g., using an ELISA technique, i.e., using an enzyme label and detecting for the presence of the label on the antibody-peptide product.

The present invention is further directed to a therapeutic method of treating Goodpasture syndrome in a patient by neutralizing Goodpasture antibodies in the whole blood or liquid fraction thereof, e.g., plasma or serum, of the patient, for example, a human patient, by contacting the whole blood or liquid fraction thereof from the patient with an effective antibody neutralizing amount of a peptide having no more than 218 amino acids of the human α3 chain of type IV collagen comprising the following amino acid sequence: ISRCQVCMKKRH (SEQ ID NO:3). In such therapeutic method, the peptide is preferably bound to a solid support and the blood, serum or plasma from the patient passes over the peptide bound to the solid support, whereby the peptide captures the Goodpasture antibodies to remove such antibodies from the patient's blood, serum or plasma. The blood, serum or plasma with some, all or most of the Goodpasture antibodies removed is then returned to the bloodstream of the patient intravenously.

BRIEF DESCRIPTION OF THE DRAWINGS

FIG. 6 is a Western blot analysis of the reactivity of Goodpasture antigen (α3NC1 Monomer) with the peptide bound GP antibodies from a cynogen bromide activated Sepharose 4B column. 1 mg of α3 peptide was coupled to the matrix for 12 hours upon packing it on a column, GP sera (1:10 dilution) was repeatedly passed through the column for 5 times and the non-specifically bound antibodies removed, upon which the bound antibodies were eluted at low pH and immediately neutralized and dialysed against 1×PRS pH 7.4. This sample was then used for a Western blot analysis.

FIG. 7 depicts oligonucleotide primer sequences. N is A or C or G or T. Numbers in parentheses at the right indicate the number of the α3(IV) amino acid from which the 5' end of the nucleotide sequence was derived. The α3(IV) amino acid sequence is from reference 13, numbering the first glycine residue of M2* as 1. Numbers in brackets at the right indicate the number of the α1(IV) nucleotide from which the 5' end of the nucleotide sequence was derived. The α1(IV) sequence is from reference 29.

|  | SEQUENCE | SEQ. ID. NO. |
| --- | --- | --- |
| F1: | 5'-AAGCCNGGNGA(C,T)ACAGG-3' | 4 |
| F2: | 5'-AAGCCNGGNGA(C,T)ACCGG-3' | 5 |
| F3: | 5'-AAGCCNGGNGA(C,T)ACGGG-3' | 6 |
| F4: | 5'-AAGCCNGGNGA(C,T)ACTGG-3' | 7 |
| R1: | 5'-TA(A,G)TG(T,C)CTNGT(A,G)AANACAAA-3' | 8 |
| R2: | 5'-TA(A,G)TG(T,C)CTNGT(A,G)AANACGAA-3' | 9 |
| R3: | 5'-TA(A,G)TGNCGNGT(A,G)AANACAAA-3' | 10 |
| R4: | 5'-TA(A,G)TGNCGNGT(A,G)AANACGAA-3' | 11 |
| FA: | 5'-GCNGGNCGNGTNATGCG-3' | 12 |
| FB: | 5'-GCNGGNCGNGTNATGAG-3' | 13 |
| FC: | 5'-GTNTT(C,T)ACNAG(A,G)CA(C,T)TATC-3' | 14 |
| FD: | 5'-CCAGG(A,C)GA(C,T)AC(A,C,T)GGNCC(A,C,T)CCAG-3' | 15 |
| RA: | 5'-CAGGAAGGGCAT(G,T)GTGCTGAA-3' | 16 |

-continued

| SEQUENCE | SEQ. ID. NO. |
|---|---|
| RB: 5'-GG(G,C)GCCTCACACACAG(A,C)ACA-3' | 17 |
| RC: 5'-TTGCAG(A,T)ACAGGAAGGGCAT-3' | 18 |
| RD: 5'-TTGCAG(A,T)ACAGGAAGGG-3' | 19 |
| F9*: 5'-CCCGATGGGTTGCCAGGATCCAT-3' | 20 |
| R9*: 5'-TGACTATGCCTGGTCACAAG-3' | 21 |

Figure 8A:
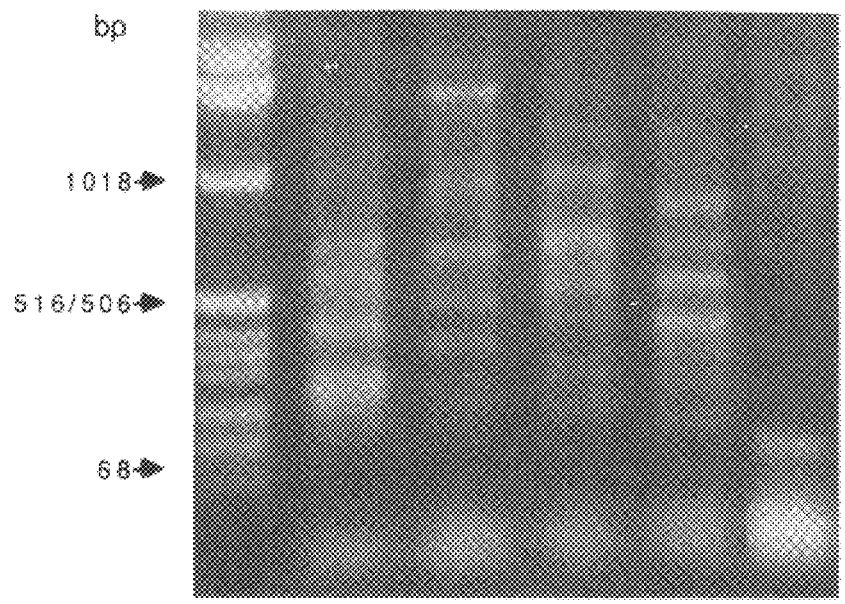

FIG. 8A depict blots concerning

PCR reaction products obtained using a bovine genomic template. The primers used are indicated below each lane. F9* and R9* are primers complementary to corresponding regions of human α1(IV). Arrows mark the positions of the 1018 and 516\1506 bp marker fragments (lane M) and the expected position of a 68 bp fragment. PCR conditions: denature 94° C.; 1 min: anneal 60° C.; 15 secs: extend 72° C.; 30 secs (30 cycles).

Figure 8B:
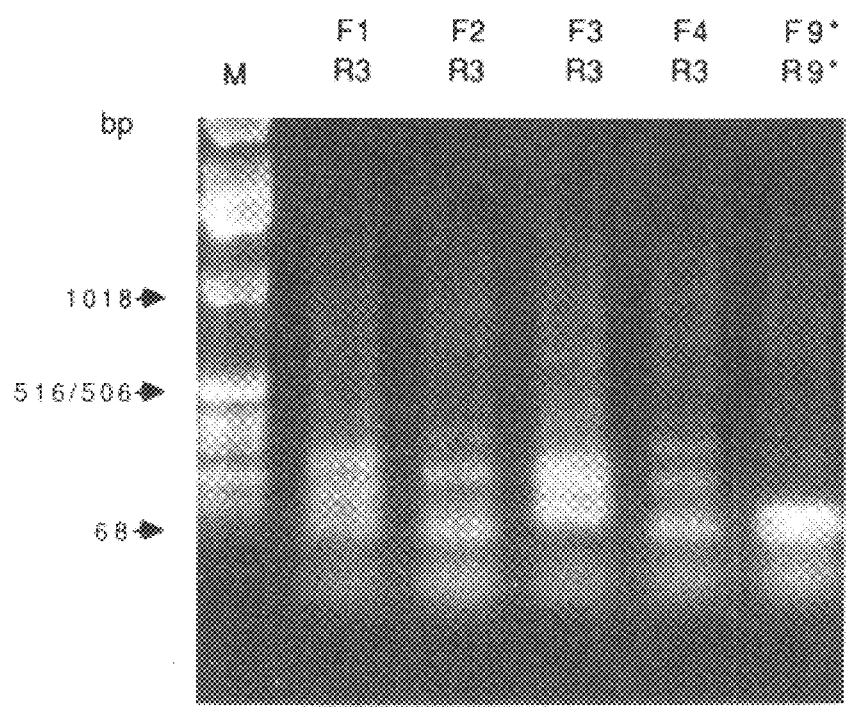

FIG. 8B depicts blots concerning reactions identical to those in FIG. 8a except for the PCR cycling profile: denature 94° C; 1 min, anneal 68° C.; 30 secs (2 cycles): denature 94° C.; 1 min, anneal 66° C.; 30 secs (2 cycles): denature 94° C.; 1 min, anneal 64° C.; 30 secs (2 cycles): denature 94° C.; 1 min, anneal 58° C. for 28 cycles.

Figure 9:
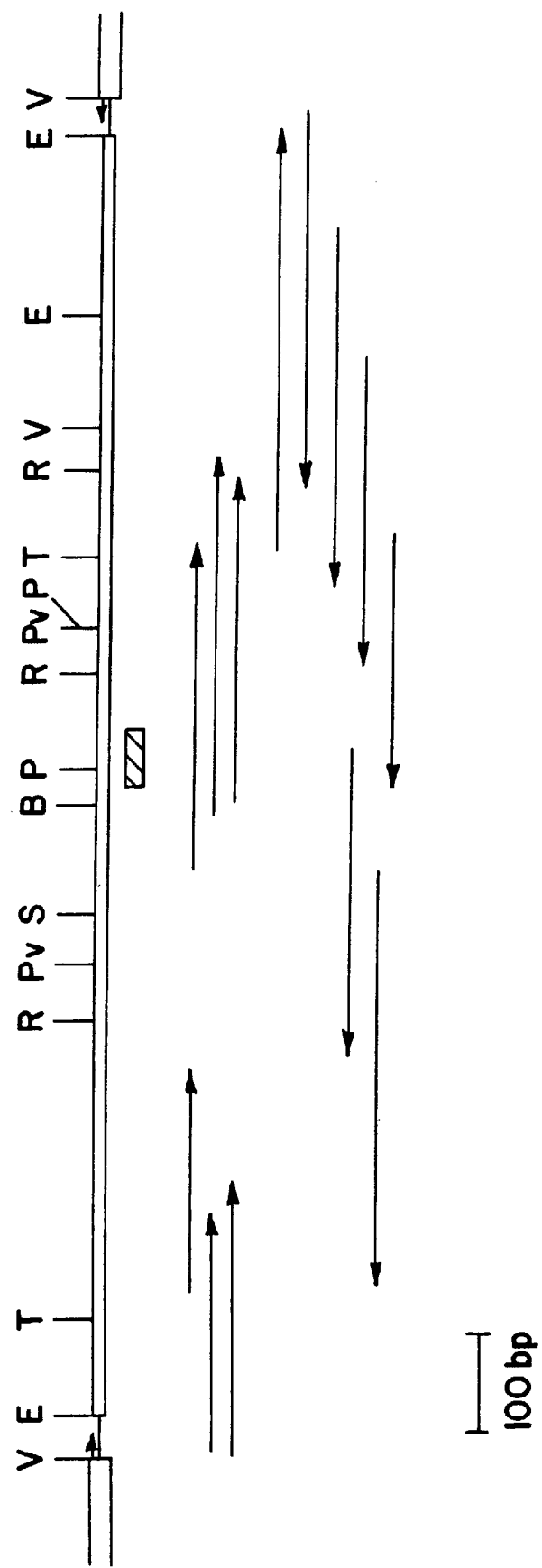

FIG. 9 is a restriction map and sequencing strategy for KEMC15. cDNA from KEMC15 is represented by the solid tick line, pbluescript by the open-ended hollow bars and λgt11 by the solid thin line. Solid arrows indicate the length and orientation of sequence analysis. Open arrows(→) show the position of the λgt11 primers used to amplify the CDNA library insert. The position of the probe KEM68 is shown by a hatched box. Restriction sites for BamHI (B), EcoRI (E), EcoRV(V), PstI,(P), PvuII(Pv), RsaI(R), SmaI(S) and TaqI (T) are indicated.

DETAILED DESCRIPTION OF THE INVENTION

The present invention concerns a novel type IV collagen, α3(IV) isolated from human and bovine basement membranes. The noncollagenous (NC1) domain of α3(IV) is of particular interest as it appears to be the component of the basement membrane which reacts maximally with the Goodpasture antibody. The cloning and sequencing of a cONA encoding 218 residues of the NC1 domain of the human α3(IV) chain, COL4A3 is described herein and will permit further study of the nature of the Goodpasture epitope. It will allow in vitro synthesis of the epitope, for use in diagnostic screening and for adsorption of pathogenic antibody for treatment of the disorder. Of further interest is the possible role of abnormalities of the α3(IV) chain in Alport syndrome, as suggested by immunological and chemical data. To determine whether α3(IV) may be mutated in Alport syndrome, applicants localized the COL4A3 gene, by somatic cell hybrid analysis and in situ hybridization of metaphase to chromosome 2.

Mutations in α3(IV) cannot therefore be responsible for the vast majority of cases of Alport syndrome, which have been shown to be X-linked. One explanation for the immunochemical data is that mutations of the α5(IV) chain, which has been localized to Xq22 and found to be mutated in at least 3 kindreds with Alport syndrome, lead to failure to incorporate the α3(IV) chains into the multimeric structure of glomerular basement membrane.

It remains to be determined whether AS (Alport syndrome) mutations are confined to the α5(IV) chain or whether they also involve other type IV collagens as suggested by the immunochemical data. Applicants therefore cloned the gene encoding the α3(IV) chain as a step towards characterizing the Goodpasture antigen and determining the possible role of mutations of α3(IV) in Alport syndrome. Using the polymerase chain reaction (PCR) with primers derived from each end of the known 27 amino acid residue bovine α3(IV) protein sequence, a 68 bp bovine genomic fragment was amplified (Morrison et al. 1991). This fragment was then used to probe a bovine lens CDNA library and a 1.5 kb partial cDNA clone obtained. This encodes 238 residues of the triple helical collagenous domain and all 233 residues of the NC1 domain of the α3(IV) chain. As described here, this bovine cDNA clone was used to screen a human kidney cONA library and a 2.7 kb human cONA clone obtained. This clone encodes 218 residues of the NC1 domain and a portion of the 3' untranslated region of the human α3(IV) chain. Applicants have mapped this gene using somatic cell hybrids and by in situ hybridization. These techniques localize the COL4A3 gene to chromosome 2. Clearly, as the majority of cases of Alport syndrome are X-linked, mutations in COL4A3 cannot be responsible for the disorder in these patients. A mechanism whereby mutations in COL4A5 could lead to a failure to incorporate the α3(IV) chain into heterotrimers and hence into the 3-dimensional structure of basement membrane, is proposed.

The NC1 domains of type IV collagen can be excised from the basement membrane by cleavage with bacterial collagenase. The excised domains exist as hexamers, which can be separated by denaturing polyacrylamide gel electrophoresis to yield a number of monomeric and dimeric species (Butkowski et al. 1985). Maximal reactivity to serum containing Goodpasture antibody resides in the subunit Mr=28,300, designated M28+++ in human tissue or M2* in bovine tissue (Butkowski et al. 1985; Wieslander et al. 1985). This subunit has been taken to be the NC1 domain of a novel type IV collagen, α3(IV), as it has many physical features in common with the abundant α1(IV) and α2(IV) chains, yet is clearly distinct from them (Hudson et al. 1989).

Short portions of the junctional region between the collagenous and NC1 domain of the α3(IV) chain have been sequenced in both human and bovine tissue (Saus et al. 1988; Butkowski et al. 1990). Using a PCR based strategy, with orimers derived from the short bovine α3(IV) peptide sequence, applicants have cloned partial cDNAs encoding the NC1 domain of the bovine α3(IV) chain (Morrison et al. 1991) and used the bovine/human homology to clone and localize the 3' end of the human α3(IV) chain.

The amino acid sequence of α3(IV) derived from the clone KMC27 will allow further investigation of the nature of the Goodpasture epitope. It will also be of value in the design of improved assays for the specific Goodpasture antibody. At present, assays for Goodpasture syndrome rely on a crude collagenase digest of GBM. This yields occasional false positive results, as patients with other forms of nephritis develop circulating antibodies to a variety of basement membrane components, secondary to other disease processes. For example, patients with IgA nephropathy develop immune complexes containing fibronectin and IgA that bind to the triple helical domain of type IV collagen (Cederholm et al. 1988); several patients with poststreptococcal glomerulonephritis have circulating antibodies against the 7S domain of type IV collagen and heparan sulphate proteoglycan (Fillit et al. 1985; Kefalides et al. 1986). The sequence data given here will be used to design synthetic peptides that will specifically detect anticollagen—α3(IV). Such peptides can also be used for adsorption of the pathogenic antibody, offering a novel treatment option for Goodpasture syndrome.

Attention has also been focussed on the possible role of mutations of the α3(IV) chain in Alport syndrome. Several investigators have found that binding of Goodpasture antibody to GBM is frequently absent in patients with this disease, as determined by immunofluorescence of GBM tissue sections (Olsen et al. 1980; Jenis et al. 1981; Jeraj et al. 1983; Kashtan et al. 1986). Absent or reduced binding of a monoclonal antibody directed towards the Goodpasture antigen has also been shown in renal biopsies from 10 Alport patients (Savage et al. 1986). In renal addition, immunochemical and chemical evidence for the absence of the collagenase solubilized human Goodpasture antigen, M28+++, in the GBM of 3 patients with X-linked Alport syndrome, has been obtained (Kieppel et al. 1987). Others however, report a partial, rather than complete loss of the Goodpasture antigen in GBM sections from affected individuals (McCoy et al. 1982).

There is evidence, however, that suggests that an abnormality of the α3(IV) chain may not be the primary defect in Alport syndrome. Recently the gene encoding a further novel collagen chain, α5(IV), has been cloned, mapped to the Xq22 region and found to be mutated in at least 3 of 18 kindreds with this heterogeneous disorder (Hostikka et al. 1990; Myers et al. 1990). Several investigators have reported Alport patients who, on transplantation, develop antibodies to a 26 kD protein, rather than to the 28 kD protein expected if such antibodies were targeted to the NC1 domain of the α3(IV) chain (Kashtan et al. 1986; Savage et al. 1989). The estimated size of the α5(IV) NC1 domain is 26 kD, and may well represent the target of the the post-transplantation antibodies. Kleppel et al. (1989) have shown that both a post-transplantation antibody which recognizes the 26 kD protein, and an antibody to the 28 kD protein show an identical binding pattern to the glomerular basement membrane of a female heterozygote with Alport syndrome, consistent with random inactivation of the X chromosome.

To understand the molecular pathology of Alport syndrome, one must explain why α3(IV) is not found in the GBM of patients with the X-linked form of the disease, which at least in some cases is produced by an α5(IV) mutation. One hypothesis was that the α3(IV) and α5(IV) chains are both encoded on the X chromosome, perhaps in a head-to-head arrangement such as that observed for the α1(IV) and α2(IV) genes on chromosome 13 (Poschl et al. 1988)). As we have shown here, the gene encoding the NC1 domain of α3(IV) maps to the 2xx region. Therefore, mutations in α3(IV) cannot be responsible for the majority of cases of Alport syndrome, which are clearly X-linked (Atkins et al. 1988; Brunner et al. 1988; Flinter et al. 1988). Whether mutations in the α3(IV) chain are responsible for those cases of Alport syndrome which are said to be autosomal remains to be determined.

How then can the immunological and chemical data implicating an abnormality in the α3(IV) chain in patients with X-linked Alport syndrome be explained? One hypothesis is that, in the presence of certain but not all mutations of α5(IV), the α3(IV) chain is not stably incorporated into heterotrimers, and thence into the basement membrane. If so, one would expect that a subset of α5(IV) mutations reduce or abolish the incorporation of the α3(IV) chain (and thus reactivity to the Goodpasture antibody), while others do not affect α3(IV) chain incorporation, and thus reactivity to the Goodpasture antibody is preserved. If the defect is one of stable incorporation of α3(IV) chains into heterotrimers in the presence of α5(IV) mutations, rather than an abnormality of the α3(IV) chain per se, then transcription of COL4A3 should be normal in the kidneys of individuals with X-linked Alport syndrome.

Maximal reactivity to serum containing Goodpasture antibody resides in the subunit Mr=28,300, designated M2* in bovine tissue and a similarly sized subunit, M28+++, in human tissue (Butkowski et al, (1985), *J. Biol. Chem.,* 260, 3739–3747; Wieslander et al, (1985), *J. Biol. Chem.,* 260, 8564–8570).

M2* has been isolated from bovine GBM (glomerular basement molecule) and LBM (lens basement molecule), and a short portion of the M2* peptide from LBM has been sequenced (Saus et al, (1988) *J. Biol. Chem.,* 263, 13374–13380). M2* has been taken to be the NC1 domain of a novel type (IV) collagen, α3(IV), as it is clearly distinct from the abundant α1(IV) and α2(IV) chains, and yet has many features in common with them. It exists in monomeric and dimeric forms, has a similar molecular weight and, based on immunoprecipitation studies, is an integral component of the NC1 (noncollagenous) hexamer of collagen IV. The short amino acid sequence of α3(IV) available from the collagenous/NC1 junction reveal ed Gly-Xaa-Yaa triplets at the amino terminus end together with 13 residues of the NC1 domain, 8 of which were identical to the residues in the same region of the α1(IV) chain.

Disclosed herein is a PCR strategy used to clone a portion of the bovine α3(IV) gene. Degenerate oligonucleotide primers complementary to each end of the short portion of the known M2* peptide sequence were used in the PCR (polymerase chain reaction) to amplify a 68 base pair bovine geromic fragment. PCR cycles were performed using a high (68° C.) annealing temperature at first, with a stepwise reduction (1° or 2° C.) in annealing temperature in subsequent cycles. In this way, although the amount of primer bound to the template during the initial amplification cycles is small, exactly complementary primer/template interactions represent a higher proportion of the total primer/template interactions than that which occurs at lower annealing temperatures. Therefore amplification of the desired target is favored. The small 68 base pair fragment thus obtained, KEM68, was then used to probe a bovine lens cDNA library. A 1.5kb partial cDNA clone (pKEMC15) which encodes 471 amino acid residues of the bovine α3(IV) chain was obtained.

Comparative sequence analyses—Analysis of the pKEMC15 sequence reveal s features common to all type (IV) collagen chains characterized to date. Within the 238 residues of the triple helical region encoded by pKEMC15 there are 3 imperfections in the regular Gly-Xaa-Yaa repeat sequence which coincide with interruptions in the corresponding regions of the α1(IV) and α2(IV) chains. In the 233 residues of the NC1 domain there are 12 conserved cysteine residues in identical positions to those in the other type (IV) collagens. There are several extended regions of sequence identity to these other chains and 71%, 61% and 70% overall homology with the human α1(IV), α2(IV) and α5(IV) chains. Therefore the results herein which provide the complete sequence of M2* and much of the collagenous domain of its parent molecule, support its previous designation as a type (IV) collagen.

Butkowski et al, (1990), *J. Lab. Clin. Med.*, 115, 365–373, have recently sequenced a portion of the human M28+++ peptide which was obtained from collagenase digestion of human GBM. Of the 13 residues characterized by amino acid analysis, 12 are identical to the equivalent portion of the bovine sequence obtained from pKEMC15. Furthermore, the amino acid composition of the bovine α3(IV) NC1 domain predicted from the nucleotide sequence is very similar to that obtained from previous peptide sequencing of the human M28+++ fragment. This thus adds further evidence for the equivalence of the bovine M2* and human M28+++ fragments.

References

1. TimpI, R., Wiedemann, H., Van Delden, V., Furthmayr, H., and Kuhn, K. (1981) *Eur. J. Biochem.* 120, 203–211
2. Martin, G. R., TimpI, R., and Kuhn, K. (1988) *Adv. Protein Chem.* 39, 1–50
3. TimpI, R., (1989) *Eur. J. Biochem.* 180, 487–502
4. Hostikka, S. L., and Tryggvason, K. (1988) *J. Biol. Chem.* 263, 19488–19493
5. Soininen, R., Haka-Risku, T., Prockop, D. J., and Tryggvason, K. (1987) *FEBS Lett.* 225, 188–194
6. Muthukumaran, G., Blumberg, B., and Kurkinen, M. (1989) *J. Biol. Chem.* 264, 6310–6317
7. Saus, J., Quinones, S., Mackrell, A.,Blumberg, B., Muthukumaran, G., Pihlajaniemi, T., and Kurkiven, M. (1989) *J. Biol. Chem.* 264, 6318–6324
8. Blumberg, B., MacKrell, A. J., and Fessier, J. H. (1988) *J. Biol. Chem.* 263, 18328–18337
9. Butkowski, R. J., Wiesiander, J., Wisdom, B. J., Barr, F., Noelkan, M. E., and Hudson, B. G. (1985) *J. Biol. Chem.* 260, 3739–3747
10. Wieslander, J., Langeveld, J., Butkowski, R., Jodlowski, M., Noelken, M., and Hudson, B. G. (1985) *J. BioL Chem,* 260, 8564–8570
11. Butkowski, R., Langeveld, J. P. M., Wieslander, J., Hamilton, J., and Hudson, B. G. (1987) *J. Biol. Chem.* 262, 7874–7877
12. Butkowski, R., Shen, G-Q., Wieslander, J., Michael, A. F., and Fish, A. J. (1980) *J. Lab. Clin. Med.* 115, 365–373
13. Saus, J., Wieslander, J., Langeveld, J. P. M., Quinones, S., and Hudson, B. G. (1988) *J Biol. Chem.* 263, 13374–13380
14. Hudson, B. G., Wieslander, J., Wisdon, B. J. Jr., and Noelken, M. G. (1989) *Lab. Invest.* 61, 256–269
15. Kleppel, M. M., Michael, A. F. and Fish, A. J. (1986) *J. BioL Chem.* 261, 16547–16552
16. Jeraj, K., Kim, Y., Vernier, R. L., Fish, A. J., and Michael, A. F. (1983) *Am. J. Kidney Dis. II,* 626–629
17. Kashtan, C., Fish, A. J., Kleppel, M., Yoshioka, K., and Michael, A. F. (1986) *J. Clin. Invest.* 78, 1035–1044
18. Kleppel, M. M., Kashtan, C. E., Butkowski, R. J., Fish, A. J., and Michael, A. F. (1987) *J. Clin. Invest.* 80, 263–266
19. Jenis, E. H., Val eski, J. E., Calcagno, P. L. (1981) *Clin. Nephrol.* 15, 111–114
20. Olson, D. L., Anand, S. K., Landing, B. H., Heuser, E.,Grushkin, C. M., and Lieberman, E. (1980) *J. Pediatr.* 96, 697–699
21. Savage, C. O. S., Pusey, C. D., Kershaw, M. J., Cashman, S. J., Harrison, P., Hartley, B., Turner, D. R., Cameron, J. S., Evans, D. J., and Lockwood, C. M. (1986) *Kidney Int.* 30, 107–112
22. Hostikka, S. L, Eddy, R. L., Byers, M. G., Hoyhtya, M., Shows, T. B., and Tryggvason, K., (1990) *Proc. Natl. Acad. Sci. U.S.A.* 87, 1606–1610
23. Myers, J. C., Jones, T. A., Pohjolainen, E-R., Kadri, A. S., Goddard, A. D., Sheer, D., Solomon, E., and Pihlajaniemi, T. (1990) *Am. J. Hum. Genet.* 46, 1024–1033
24. Atkin, C. L., Hasstedt, S., Menlove, L., Cannon, L., Kirschner, N., Schwartz, C., Nguyenk, K. and Skolnick, M. (1988) *Am. J. Hum. Genet.* 42, 249–255
25. Brunner, H., Schroder, C., van Bennekom, C., Lambermon, E., Tuerlings, J., Menzel, D., Olning, H., Monnens, L., Wieringa, B. and Ropers, H.-H.(1988) *Kidney Int.* 34, 507–510
26. Szpiro-Tapia, S., Bobrie, G., Guilloud-Bataille, M., Heuertz, S., Julier, C., Frezal, J., Grunfeld, J. P. and Hors-Cayla, M. C. (1988) *Hum. Genet.* 81, 85–87
27. Flinter, F. A., Abbs, S., and Bobrow, M. (1988) *Genomics* 4, 335–338
28 Barker, D. F., Hostikka, S. L., Zhou, J., Chow, L. T., Oliphant, A. R., Gerken, S. C., Gregory, M. C., Skolnick, M. H., Atkin, C. L., and Tryggvason, K. (1990) *Science* 248, 1224–1227
29. Pihlajaniemi, T., Tryggvason, K., Myers, J. C., Kurkinen, M., Lebo, R., Cheung, M-C., Prockop, D. J., and Boyd, C. D. (1985) *J Biol. Chem.* 260, 7681–7687
30. Gunwar, S., Saus, J., Noelken, M. E., and Hudson, B. G. (1990) *J. Biol. Chem.* 265, 5466–5469
31. Grunfeld, J-P. (1985) *Kidney Int.* 27, 83–92
32. Hinglais, N., Grunfeld, J-P., Bois, E. (1972) *Lab. Invest.* 27, 473–487
33. Yoshikawa, N., Cameron, A. H., White, R. H. R. (1981) *J. Pathol* 135, 199–209

Expression

The general nature of vectors for use in accordance with the present invention is not crucial to the invention. In general, suitable vectors and expression vectors and constructions therefor will be apparent to those skilled in the art.

Suitable expression vectors may be based on phages or plasmids, both of which are generally host-specific, although these can often be engineered for other hosts. Other suitable vectors include cosmids and retroviruses, and any other vehicles, which may or may not be specific for a given system. Again, control sequences, such as recognition, promoter, operator, inducer, terminator and other sequences essential and/or useful in the regulation of expression, will be readily apparent to those skilled in the art. The vectors may be modified or engineered in any suitable manner.

In general, there are a number of methods which can be used to produce the peptide and nucleotide sequences of the invention. One straightforward method is simply to synthesize the appropriate nucleotide sequence, insert it into a suitable expression plasmid, transform a suitable host, culture the host, and obtain the peptide of the invention by any suitable means, such as sonication and centrifugation.

Alternatively, fragments can be obtained by digestion with the relevant restriction enzymes, and a suitable oligonucleotide ligated to the 5'-end coding for the missing amino acids. The resulting cDNA can then be used as above.

Other suitable methods will be apparent to those skilled in the art.

Ideally, the receiving vector has a ClaI site and a SalI site for each of insertion, but blunt-end ligation, for example, may also be used, although this may lead to uncertainty over reading frame and direction of insertion. In such an instance, it is a matter of course to test transformants for expression, 1 in 6 of which should be useable. Suitable vectors may be selected as a matter of course by those skilled in the art according t the expression system desired.

By transforming E. coli with the plasmid obtained, selecting the transformant with ampicillin or by other suitable means, and adding tryptophan or other suitable promoter inducer such as indoleacrylic acid, the desired proteextent of expression may be expressed. The extent of expression may be analyzed by SDS polyacrylamide gel electrophoresis—SDS-PAGE (Nature, (1970), 227, pp. 680–685).

It will also be appreciated that, where another vector is used, for example, it will be equally acceptable to employ a different selection marker or markers, or an alternative method of selection, and/or to use any suitable promoter as required or convenient.

After cultivation, the transformant cells are suitably collected, disrupted, for example, sonicated, and spun-down. Disruption may also be by such techniques as enzymic digestion, using, for example, cellulase, or by shaking with an agent such as glass beads, but methods such as sonication are generally preferred, as no additions are necessary.

Conventional protein purification is suitable to obtain the expression product.

Where not specifically described herein, methods for growing and transforming cultures etc. are usefully illustrated in, for example, Maniatis (Molecular Cloning, A Laboratory Notebook, Maniatis et al. [Ed's], Cold Spring Harbor Labs, N.Y.).

Cultures useful for the invention may suitably be cultures of any living cells, and may vary from prokaryotic expression systems up to eukaryotic expression systems. One preferred prokaryotic system is that of E. coli, owing to its ease of manipulation. However, in general terms, it is preferable to express proteins intended for use in the human body in higher systems, especially mammalian cell lines. A currently preferred such system is the Chinese Hamster Ovary (CHO) cell line. Although this system tends not to be as easy to use as the E. coli system, its advantage lies in the processing of the protein after primary synthesis. E. coli, for example, does not have the equipment to glycosylate mammalian proteins, and it is preferred to glycosylate such proteins where possible, if for no other reason than that the natural proteins are glycosylated. In certain cases, glycosylation may be of no assistance whatever, and may even hinder the protein.

Other expression systems which may be employed include streptomycetes, for example, and yeasts, such as Saccharomvces spp., especially S. cerevisiae. With current progress in research, other systems are becoming available and there is no effective limit on which system is used, provided that it is suitable. The same systems may also be used to amplify the genetic material, but it is generally convenient or use E. coli for this purpose where only proliferation of the DNA is required.

Diagnostics

Labels for use in the present invention include, substances which have a detectable physical, chemical, or electrical property. When a detectable labeling substance is introduced, it can be linked directly such as by covalent bonds or can be linked indirectly such as by incorporation of the ultimately detectable substance in a microcapsule or liposome.

Labeling materials have been well-developed in the field of immunoassays and in general almost any label useful in such methods can be applied to the present invention. Particularly useful are enzymatically active groups, such as enzymes (see Clin. Chem., (1976) 22:1232, Reissue Pat. U.S. Pat. No. 31,006, and UK Pat. 2,019,408), enzyme substrates (see U.S. Pat. No. 4,492,751), coenzymes (see U.S. Pat. Nos. 4,230,797 and 4,238,565), and enzyme inhibitors (see U.S. Pat. No. 4,134,792); fluorescers (see Clin. Chem., (1979) 25:353); chromophores; luminescers such as chemiluminescers and bioluminescers (see U.S. Pat. No. 4,380,580); specifically bindable ligands such as biotin (see European Pat. Spec. 63,879) or a hapten (see PCT Publ. 83–2286); and radioisotopes such as $^3H$, $^{35}S$, $^{32}P$, $^{125}I$, and $^{14}C$. Such labels are detected on the basis of their own physical properties (e.g., fluorescers, chromophores and radioisotopes) or their reactive or binding properties (e.g., ligands, enzymes, substrates, coenzymes and inhibitors). For example, a cofactor-labeled species can be detected by adding the enzyme (or enzyme where a cycling system is used) for which the label is a cofactor and a substrate or substrates for the enzyme. Such detectable molecule can be some molecule with a measurable physical property (e.g., fluorescence or absorbance) or a participant in an enzyme reaction (e.g., see above list). For example, one can use an enzyme which acts upon a substrate to generate a product with a measurable physical property. Examples of the latter include, but are not limited to, beta-galactosidase, alkaline phosphatase and peroxidase.

EXAMPLE 1

Collagen α3(IV) Hybridization Probe

A PCR-based strategy was used to generate a bovine α3(IV) hybridization probe (Morrison et al. 1991). Degenerate sense and antisense primers were designed complementary to each end of the known 27 residue amino acid sequence of the bovine α3(IV) peptide chain. These were then used in a PCR reaction to amplify a 68 bp bovine genomic fragment (KEM68). KEM68 was then used to screen a λgt11 bovine lens cDNA library (Clontech) and a 1.5 kb partial cDNA clone obtained, encoding 238 residues of the triple helical domain and all 233 residues of the NC1 domain.

EXAMPLE 2

Screening of cDNA Library

The 1.5 kb bovine cONA clone was then used to screen an oligo-dT primed λgt10 human kidney cDNA library (Clontech), an oligo-dT primed λgt11 human kidney cONA library and a random primed human kidney cDNA library. Of 3×10⁵ clones screened in each library, only one positive clone was obtained, from the human kidney cONA library (Clontech). The secondary from this positive was eluted into 500 μl of buffer (100 mM NaCl, 8 mM MgSO47H₂O, 50 mM TrisCI, pH7.5 and 0.01% gelatin). 2 μl of this was used as a template for PCR with primers complementary to the β-galctosidase portion ot the μgt10 template. The amplified product, KMC27 was digested with EcoR1 and cloned into the EcoR1 site of pBluescript (Stratagene). The sequence was obtained using T7 polymerase (Sequenase) with T7 and T3 sequencing primers and 17-residue oligonucleotide primers designed from known sequences of the inserts, according to standard protocols.

EXAMPLE 3

Chromosomal Assignment

Southern blot hybidization of α3(IV) probe to rodent × human hybrids.

Chromosomal assignment of the human α3(IV) gene was performed using a panel of 11 human-Chinese hamster hybrids. DNA from human and Chinese hamster parental cell lines and human × rodent hybrids was digested to completion with Pst1. The DNA was fractionated by electrophoresis on a 0.9% agarose gel and blotted onto Hybond N+ (Amersham International ). A 1.7 kb 5' portion of the cDNA KMC27 was labelled with [$\alpha^{32}$P]dCTP by random primer labelling (Feinberg and Vogelstein, 1983) and hybridized to the filter bound DNAs in Church and Gilbert buffer (0.5M $Na_2HPO_4$, 7% SDS, 1% BSA, 1 mM EURA) at 65° C. The filters were then washed in 0.1% SDS and 1×SSC (0.5M NaCl, 0.015M Na Citrate, pH7.0) and exposed to film for 3 days.

Northern Analysis

Total RNA was isolated from snap-frozen bovine 60 day old calf tissues using an acid guanidinium thiocyanatelphenol/chloroform extraction procedure (Chomczynski and Sacchi, 1987). 5–10 µg was electrophoresed on a 1.2% agarose gel containing formal dehyde, blotted to nitrocellulose and hybridized with KEMC15, the bovine COL4A3 probe. Washing was in 0.1% SDS, 0.5× SCC at 65° C. and the filter exposed to film for 2 days. pA+RNA was isolated from total RNA using an oligo dT column (Collaborative Research Inc, Waltham, Mass.).

EXAMPLE 4

Isolation of cDNA Clones

To generate an α3(IV) hybridization probe, use was made of the 27 residue amino acid sequence of the bovine α3(IV) chain, as no human α3(IV) amino acid sequence was currently available (Saus et al. 1988). The polymerase chain reaction was used to amplify a 68 bp segment corresponding to the bovine sequence. A longer bovine cONA clone (KEMC15) was then obtained from a bovine line library. KEMC15 encodes 238 residues of the tripland the comegion and the complete 233 residues of the NC1 domain. Applicants anticipated that the bovine and human α3(IV) amino-acid sequences would be highly conserved in this region (Butkowski et al. (1990) have subsequently shown conservation of eleven residues in a twelve residue stretch). Therefore applicants used the bovine clone to screen for human homologs. On screening 3×10$^5$ clones of each of 3 human kidney cONA libraries with KEMC15, only 1 positive clone, KMC27, was obtained.

EXAMPLE 5

Nucleotide Sequence of α3(IV) cDNA

Sequence analysis of the cONA clone KMC27 reveal s an open-reading frame which, on translation, encodes 220 carboxy terminal residues of the NC1 domain of α3(IV) and ~2000 bp of the 3' untranslated region. As anticipated, within the coding region, the bovine and human sequences are very similar, with 90.5% homology at the nucleotide level and 93% homology at the amino acid level. Only 2 of the 15 non-identical amino acid residues are non-conservative substitutions. The homology of the sequence encoded by KMC27 with the bovine COL4A3 sequence, confirms its identity as a portion of the human COL4A3 gene. The amino acid composition of the NC1 domain of α3(IV) derived from the sequence of KMC27 is similar to that obtained from amino acid composition analysis of the human M28+++ fragment (Butkowski et al. 1990).

EXAMPLE 6

Comparative Sequence Analysis

Analysis of pKMC27 reveal s features common to all type IV collagens characterized to date. In the 220 residues of the NC1 domain there are 12 conserved cysteine residues in identical positions to those in the other type IV collagens. Overall the sequence shows 71%, 60% and 70% amino acid identity with the NC1 domains of the human α1(IV), α2(IV) and α5(IV) chains respectively It has been suggested that the NC1 domains of α1(IV) and α2(1V) are the result of an intragenic duplication, as each consists of two equal-sized internal repeats, each containing 6 cysteine residues in invariant positions (Brinker et al. 1985; Pihlajaniemi et al. 1985; Myers et al. 1987). In the α1(IV) NC1 there are 45 (out of 229) positions in which the amino acid is identical between the two halves (Brinker et al. 1985; Pihlajaniemi et al. 1985) compared with 50 positions in the α2(IV) NC1 (out of 230) and 43 in the α5(IV) NC1 (Pihlajaniemi et al. 1990). Alignment of the corresponding internal repeats in the α3(IV) chain shows that 45 amino acids are conserved between the putative duplicated halves of the NC1 domain, including all twelve cysteine residues. Of the 116 amino acid residues conserved between all 4 chains, 62 are also conserved between the 'duplicated halves' of the NC1 domain in duplications.

As Dion and Myers (1985) have speculated, the conserved elements may play a role in the assembly of triple helical molecules, while the variable regions may be operative in discriminant chain selection. This may aid in the search for that portion of the α3(IV)NC1 responsible for the Goodpasture epitope. Comparing the last 219 residues of the NC1 domains of α1(IV), α2(IV), α3(IV) and α5(IV), there are 46 positions in which the sequence of only one chain differs from the other 3; of these 46, 3 are a divergence of the α1 chain, 26 are a divergence of the α2 chain, 16 are a divergence of the α3 chain and one a divergence of the α5 chain alone. None of these divergences is duplicated, suggesting that intragenic gene duplication to form a complete NC1 domain preceded the evolution of the different type IV collagen chains.

EXAMPLE 7

Chromosomal Localization
Human×Rodent Somatic Cell Hybrids

To localize COL4A3, a panel of Chinese hamster × human somatic cell hybrids was analysed by Southern blot hybridization with a portion, KMC17, of the human KMC27 cDNA, as a probe. KMC17 detects a band of 11 kb in the Chinese hamster DNA and a band of 9 kb in the human DNA. The panel shown maps KMC17 to chromosome 2.

In Situ Hybridization

The α3(IV) gene was independantly mapped by in situ hybridization of the KMC17 cDNA clone to human metaphase chromosomes

Northern Analysis

The bovine cONA clone KMC15 which encodes 471 residues of the bovine α3(IV) chain, was used to probe a Northern blot of total RNA from bovine lung, liver and kidney. The gene codes for a single transcript of approximately 8.1 kb, the signal being equally intense in total RNA from lung and kidney, but absent in liver. Using 10 μg of polyA+ selected RNA a similar result was obtained, with similar intensity of hybridization in lung and kidney and a very faint signal obtained from liver RNA (data not shown). This is compatible with the observation that patients with Goodpasture syndrome show pathology in the lung and kidney, but no discernible liver abnormality.

EXAMPLE 8

Determination of the Molecular Structure of the GP-Autoantibody Combinign Site (Epitope).

The epitope which reacts with GP-antibodies resides on monomeric and dimeric forms of the NC1 domain of the α3 chain of type IV collagen. The epitope contains a critical disulfide bond that is required for binding of GP antibodies. Knowledge of the epitope structure will yield information required for the development of diagnostic procedures for the detection of GP antibodies and development of therapeutic procedures for the removal of the toxic GP antibodies from blood plasma.

Figure 1:
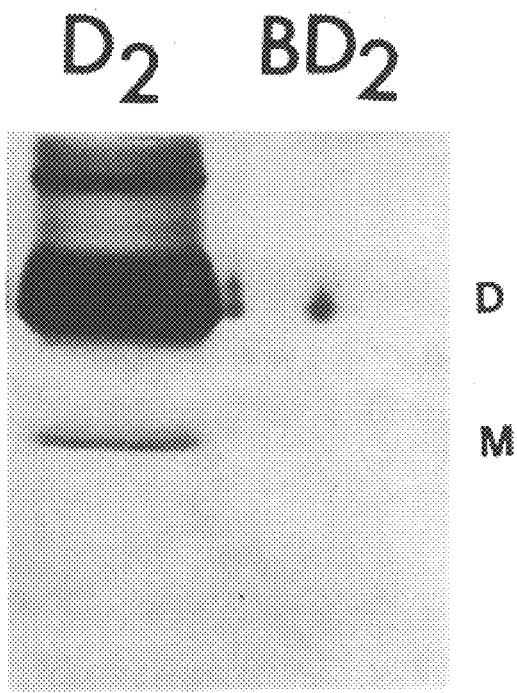
FIG. 1 is a Western blot of dimer fraction D2 (referred to in FIG. 1 as D$_2$) and NC1 hexamer before and after biotinylation samples. After biotinylation, reactivity of dimer fraction D2 with GP-antibodies is lost. Biotinylation of the native NC1 domain does not affect its reactivity with GP-antibodies indicating that the GP-epitope is sequestered inside the hexamer as previously found.

In applicants' search for the molecular identity of the GP epitope, applicants have employed mild chemical modification with a biotinylating reagent (sulfosuccinimidyl 6-biotinamido hexamoate [NHS-LC-Biotin]) which is highly specific for lysine and N-terminal amino acid residues. Lysine was selected because of the important role played by reactive amino groups in protein structure that ultimately dictates immunogenicity. The D2 fraction of NC1 hexamer, comprised of dimeric subunits reacting with GP-antibodies were biotinylated with the reagent and the products were analyzed by Western blotting with GP-sera (FIG. 1). Biotinylation abolished the reactivity of the dimeric subunits with GP sera. These results indicate that lysine is a critical residue of the epitope structure.

Figure 2:
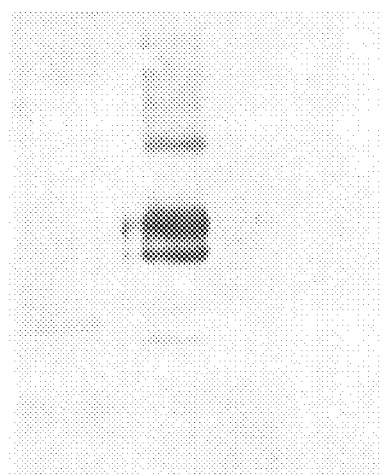
FIG. 2 is a Western Blot of the Control D1 (lane 1) and Carboxypeptidase Y treated D2 (lane 2), using GP sera.

Applicants also inventigated the influence of carboxypeptidase treatment on the reactivity of the dimer subunits with GP sera. As shown in FIG. 2, this treatment also abolished reactivity with GP sera. These results suggest that the carboxy terminus is an important element of the epitope structure.

In addition to these structural features (disulfide bond, lysine, and carboxy terminus), the epitope is expected to be distinct in amino acid sequence from an analogous region of the other known chains (α1, α2, & α5) of type IV collagen and to likely have a hydrophilic character. Based on molecular cloning studies, a region at the carboxy terminus of the NC1 domain of the α3 chain was identified that fits these five criteria. Its structure for human α3 is:

—ISRCQVCMKKRH (SEQ ID NO:3)

This 12 Mer peptide was chemically synthesized with the two cysteine residues blocked. The peptide was tested with ELISA measurements, as shown below, and found to be reactive with GP antibodies.

EXAMPLE 9

Reactivity of α3 Synthetic Peptide with GP Antibodies.

Figure 3:
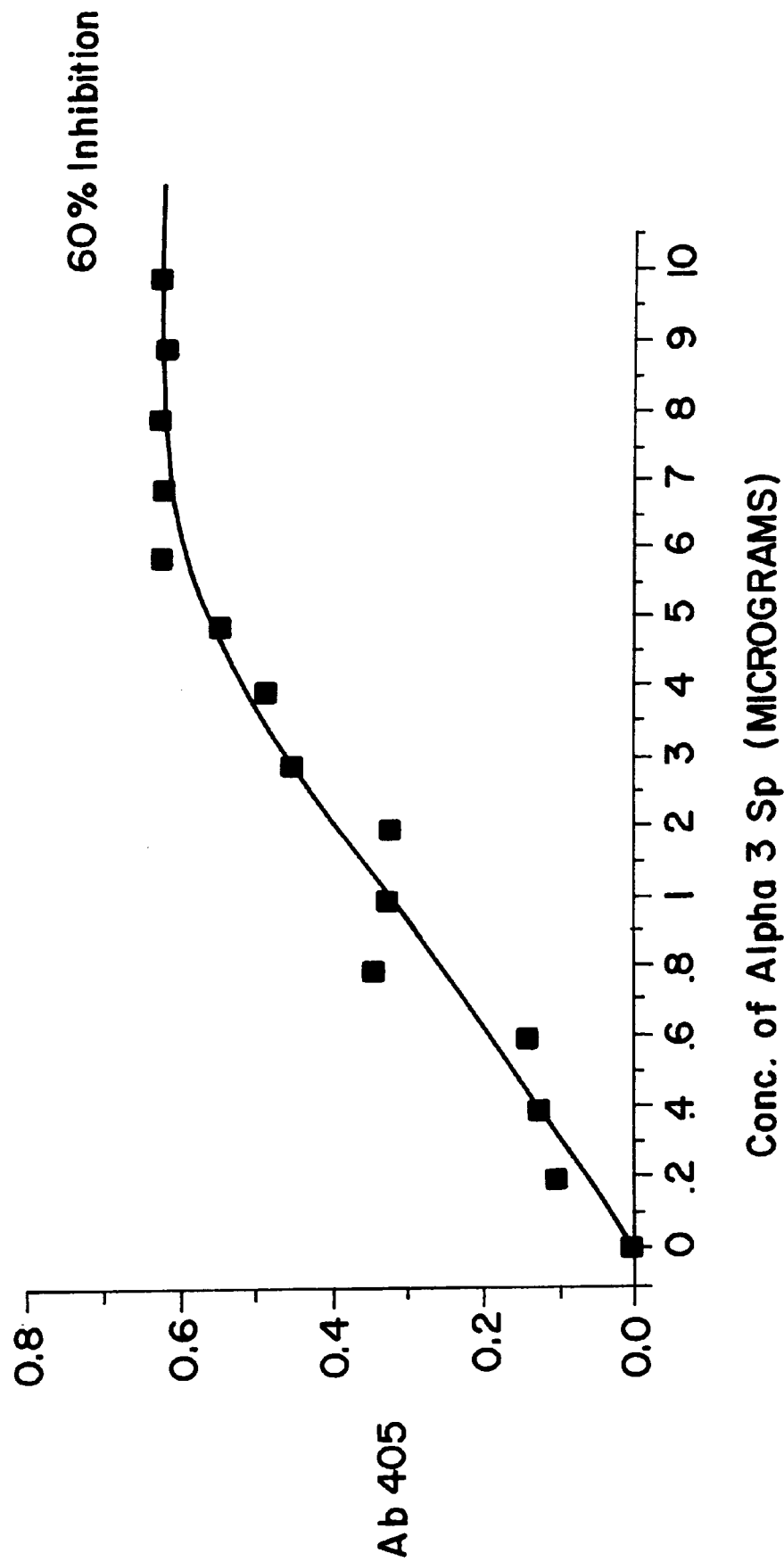
FIG. 3 is a graph depicting the results of an inhibition Elisa. The plates were coated with 400 ngs of α3NC1 monomer (Goodpasture antigen) and subsequently blocked with 1% BSA. The primary antibody was preincubated with peptide for 12 hours and then the reaction mixture was treated with the Goodpasture antigen. Secondary antibodies were against human IgG and HRP conjugated. The assay was measured at Ab 405.

The reactivity was tested with anti sera from two GP patients using two different inhibition ELISA procedures. In FIG. 3, the peptide was preincubated with GP antibodies for 12 hours and the mixture then reacted with authentic GP antigen (α3 NC1 bovine monomer). The results show 60% inhibition at saturation (peptide concentration=5.4 $10^{-6}$ molar). This information suggests that the peptide binds the GP antibody and thus represents a portion of the native epitope.

The reactivity of the peptide was also tested by another procedure where the peptide was allowed to compete with the GP antigen for binding with GP antibodies for 12 hours. The results show 42% inhibition. As control, N-terminal peptides (10 Mer) from α1, α2, α3, & α4 NC1 domains were tested for reactivitity, and the results showed no inhibition. These results further indicated that the α3 carboxy terminal peptide uniquely binds the GP antibody.

Figure 4:
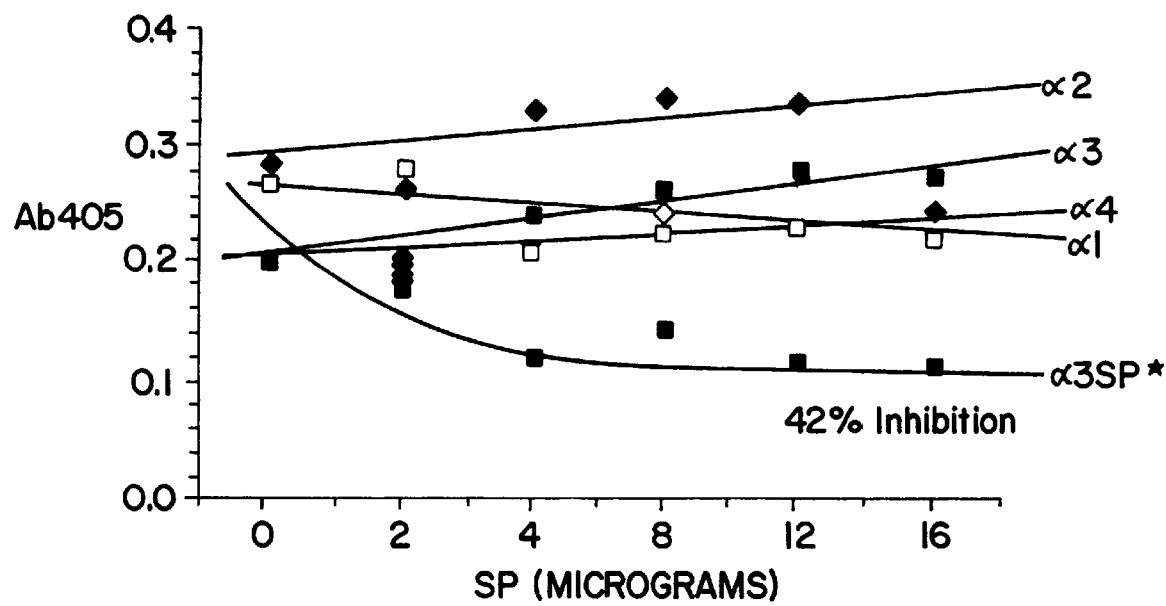
FIG. 4 is a graph depicting the results of an inhibition ELISA. The same conditions as in FIG. 3 were used, except in this case the peptide was allowed to compete with the Goodpasture (GP) antigen for GP antibodies for 12 hours.

Overall, these ELISA results indicate that the α3 carboxy terminal peptide represents a portion of the native epitope (see FIG. 4).

EXAMPLE 10

Development of Diagnostic Procedure for the Detection of GP Antibodies in Human Sera.

Figure 5:
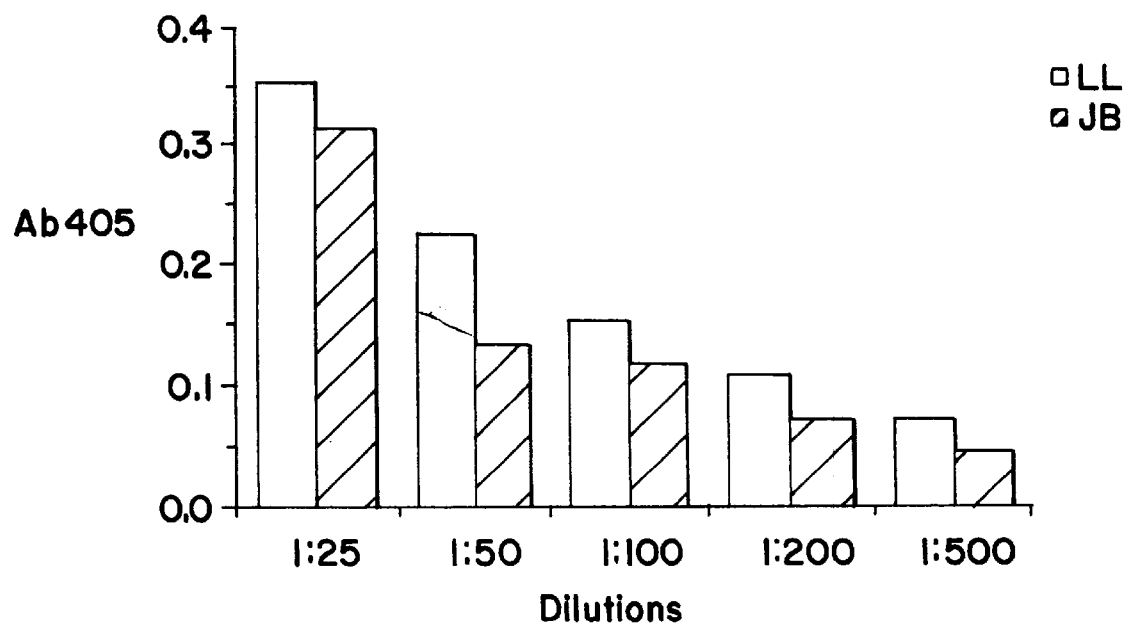
FIG. 5 is a graph which depicts the results of a direct ELISA to test the binging of Sp* to GP antibodies. The plates were coated with 20 micrograms of peptide and analyzed for its reactivity with the GP antibodies. The other conditions are same as FIG. 3.

The α3 carboxy terminal peptide was allowed to bind to ELISA plates and tested for reactivity with GP antibodies using a direct ELISA procedure. Using two GP seras, as shown in FIG. 5, the peptide bound antibody in a dose dependent manner. This indicates that the peptide can be used as a diagnostic tool for the detection of GP antibodies in blood plasma.

EXAMPLE 11

Development of a Theraphautic Procedure for the Removal of GP Antibodies from Blood Plasma.

Figure 6:
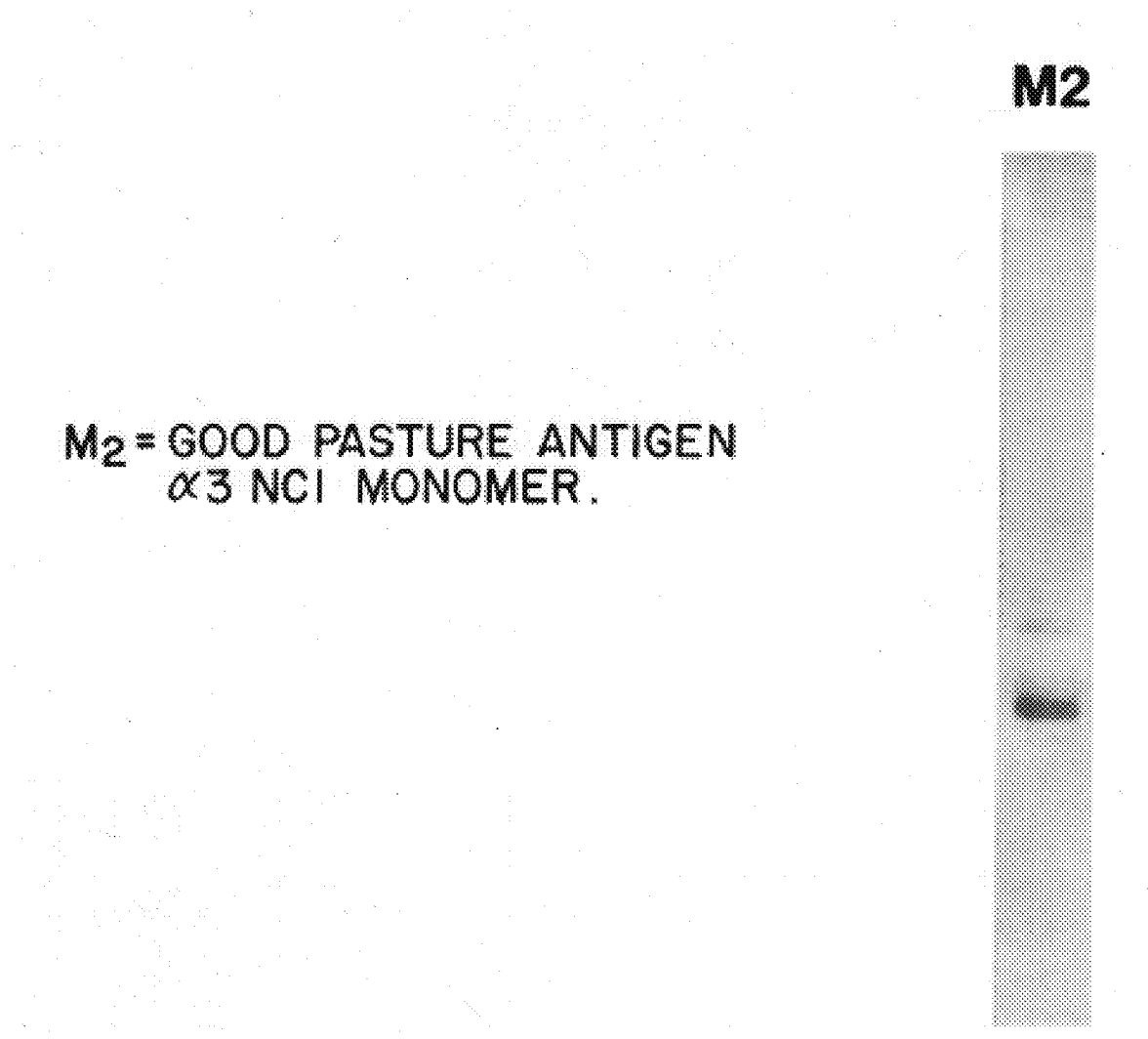

The α3 carboxy terminal peptide was bound to cyanogen bromide activated Sepharose 4B column. The column was then tested for specific binding of GP antibodies from sera. The bound antibodies were eluted and tested for reactivity with GP antigen by Western blotting (FIG. 6 ). The results show distinct reactivity with the GP antigen. This indicates that the peptide can be used to prepare a immunoabsorbent column to selectively remove toxic antibodies from blood plasma of patients with GP snydrome.

EXAMPLE 12

Primer design for the generation of collagen α3(IV) hybridization probes—Two PCR based strategies were used to generate hybridization probes. Both made use of the known 27 residue amino acid sequence of the bovine α3(IV) chain. Firstly, four degenerate sense primers (17–22 mers) were designed corresponding to regions of the known bovine α3(IV) sequence that were most distinct from the corresponding α1(IV) and α2(IV) sequences (FA,FB,FC, FD). Antisense primers were then designed to be complementary to regions of the NC1 that are highly conserved between the human and mouse α1(IV) and α2(IV) chains, in anticipation that such homology would extend to the α3(IV) chain (RA,RB,RC,RD). The second strategy involved using degenerate (32-fold) sense primers (17 mers), corresponding to the amino acids near the amino terminal end of the known 27 residue sequence of bovine α3(IV) (F1,F2,F3,F4). Similarly degenerate oligonucleotide antisense primers were also designed, corresponding to the amino acids at the carboxyl end of the known sequence (R1,R2,R3,R4) (FIG. 7).

EXAMPLE 13

PCR orotocols—Standard PCR reactions were performed in a 50 μl volume containing 10–20 ng of either bovine genomic, human genomic or human cDNA template, 25 pmols of each oligonucleotide primer, 200 µM of each dNTP, 50 mM KCl, 10 mM Tris (pH 8.3), 1.5 mM MgCl$_2$, 0.01% gelatin and 1.25 units of Tag polymerase (Perkin Elmer Cetus). Samples were overlaid with 50 µl mineral oil. Routinely, 35 cycles of PCR were performed. With primers FA-FD and RA-RD, annealing was performed at 60° C. for 1 minute, extension at 72° C. for 2 minutes and denaturation at 94° C. for 1 minute, with a final extension time of 10 minutes. With primers F1–F4 and R1–R4, annealing was for 30 seconds at 68° C. for the first cycle, at 66° C. for 30 seconds for the second, at 64° C. for 30 seconds for the third and at 58° C. for the fourth and subsequent cycles. No extension step was performed as the predicted product was only 68 base pairs. Denaturation was carried out at 94° C. for 1 minute.

EXAMPLE 14

Subcloning and sequencing—The 68 bp product obtained using primers F4 and R3 and bovine genomic template (KEM68) was cloned into the EcoRV site of the phagemid pBluescript II (Stratagene). The double-stranded plasmid, pKEM68, was sequenced using T7 polymerase (Sequenase) with T7 and T3 sequencing primers according to standard protocols.

EXAMPLE 15

Screening of cDNA library—KEM68 was labelled by PCR. A 50 µl reaction was performed containing 5 pmoles of primers F3 and R4, 50 pg of pKEM68, 10 µM dATP, dGTP, dTTP and 9.4 µM dCTP. 10 µl of [α-$^{32}$P]dCTP (3000 Ci/mmol) was added to give a final concentration of 0.6 µM. Standard buffer and 1 unit of Ta µ polymerase were used and 30 cycles of amplification performed. The reaction product was passed through a G25 column to remove most of the unincorporated primers. The labelled product was used to screen a λgt11 bovine lens cDNA library (Clontech). A total of 3×10$^5$ clones were screened and 16 positives obtained. Secondaries from these positives were eluted into 500 µl of buffer (100 mM NaCl, 8 mM MgSO$_4$7H$_2$O, 50 mM TrisCl, pH7.5 and 0.01% gelatin). 2 µl of eluant was used as a template for PCR with primers complementary to the β-galactosidase portion of the λgt11 template. The largest of the 16 amplified products, KEMC15, was sequenced directly using the same λgt11 primers as in its initial amplification. KEMC15 was subsequently cloned into the EcoRV site of pBluescript II (Stratagene). The complete sequence was obtained using 17-residue oligonucleotide primers designed from known sequences of the insert (FIG. 9).

EXAMPLE 16

Collaaen α3(IV) hybridization orobe—The known 27 residue amino acid sequence of the junction between the collagenous and NC1 domains of bovine α3(IV) was used to generate an α3(IV) hybridization probe (Saus et al, (1988) *J Biol. Chem.*, 263, 13374–13380). As the number of nucleotide sequences that may encode this peptide segment is very large, highly degenerate oligonucleotide probes would be required to include all coding possibilities. Consequently, two PCR based strategies were adopted.

In the first approach, primers were designed to correspond to regions of the known 27 amino acid sequence of bovine α3(IV) that is most distinct from the corresponding portion of α1(IV) and α2(IV) (FA-FD). On this basis, the most suitable sense primers corresponded to the carboxy terminal region of the known sequence, allowing no room for an antisense primer to be designed complementary to the known residues. Therefore, use was made of the number of highly conserved stretches of 6–7 amino acids in the NC1 domain of α1(IV) and α2(IV), which are also conserved between species. If such sequences represent essential structural elements of type (IV) collagen, it might be assumed that such homology would extend to α3(IV). 17–20 mers (RA-RD) complementary to portions of these conserved regions were therefore designed. Where α1(IV) and α2(IV) differed in these regions, a degenerate oligonucleotide was synthesized. By intention, the maximum degeneracy of these antisense primers was only 4-fold. Using various combinations of primers FA-FD and RA-RD and standard PCR protocols, products of the "correct" size were obtained using a human cDNA template, and discrete products of various sizes obtained using either human or bovine genomic templates. However, sequence analysis of these products revealed them to be portions of genes encoding α1(IV), or α2(IV).

A second strategy was therefore adopted which did not rely on the assumed homology of regions of the NC1 domain of α3(IV) with α1(IV) and α2(IV). In this approach, sense and antisense primers were designed complementary to each end of the known 27 amino acid protein sequence. As the peptide sequence is so short, there was little latitude in the design of these primers. The 3'ends of the primers had to be as distinct as possible from the corresponding regions of α1(IV) and α2(IV), to avoid amplification of these known collagen genes. Four sense primers, F1–F4, were synthesized according to the amino acid sequence lys-pro-gly-asp-thr-gly (SEQ ID NO:22), near the amino terminal end of the known sequence. AAG was used for lysine, based on codon usage frequencies in collagens. All codons for proline, glycine and asparagine were included. Four separate sense primers were synthesized, each using a different nucleotide as the wobble base of threonine, to eliminate degeneracy from the five nucleotides at the 3' end of the primers. Antisense primers were synthesized complementary to the amino-acid sequence tyr-his-arg-phe-ala-val-phe (SEQ ID NO:23), near the carboxy terminus of the peptide sequence. Again, four primers were made to eliminate degeneracy from the five 3'most nucleotides. Two of the primers (R1 and R2) incorporated the complement of the codons CG(A/C/G/T) for arginine, and two (R3 and R4), the complement of AG(A/G) for arginine (FIG. 7).

Standard 3-step PCR protocols (denature, anneal, extend) and combinations of the degenerate primers F1–F4 and R1–R4 did not yield an amplification product of the correct (predicted) size from a bovine or human genomic template or human cDNA template. The use of degenerate primers precludes the calculation of a specific predicted annealing temperature and therefore, experiments were performed with a range of annealing temperatures. Despite the use of stringent annealing temperatures and short (15 sec) annealing times, in practice many products of up to 2000 base pairs in size were generated. In an attempt to reduce the complexity of the PCR products, a PCR cycling profile with stepwise reductions in annealing temperature was adopted. The goal of the stepwise protocol is to reduce spurious amplification products during early cycles. Once a double-stranded product has been formed by PCR, regardless of the match between primer and template, that product is a perfect template for primer annealing in subsequent cycles. The use of high initial annealing temperatures reduces spurious binding of primer and increases the proportion of correct annealing, but does so at the expense of the efficiency of generation of 'correct' product. After early cycles of stringent amplification have increased the proportion of desired product in the mix, subsequent reduction of the annealing temperature allows a more efficient amplification to occur.

FIG. 8a shows an example of the PCR products obtained using combinations of the primers F1–F4 and R3, using a standard PCR cycling profile. No product of 68 base pairs is evident in any of the reactions using the degenerate primers. As FIG. 8b shows, by reducing the annealing temperature in a stepwise fashion, a 68 base pair product is clearly obtained when primers F2 and R3 or F4 and R3 are used. For non-degenerate primers, such as F9* and R9*, which are exactly complementary to portions of α1(IV), the "correct" product is obtained using both cycling profiles.

EXAMPLE 17

Nucleotide sequence of α3(IV) cDNA—The 68 base pair fragment obtained using primers F4 and R3 and bovine genomic template, KEM68, was then cloned. Sequence analysis of pKEM68 reveal ed an open reading frame which, on translation, codes for a peptide sequence identical to the known peptide sequence of α3(IV). A bovine lens cDNA library was then screened with KEM68 yielding 16 positive clones of 0.5–1.5 kb. A partial restriction map of the longest clone, pKEMC15, is shown in FIG. 9. DNA sequencing of pKEMC15 showed that the clone codes for the known α3(IV) amino acid sequence with the exception of a serine-for-tyrosine substitution at the 15th amino acid of the NC1 domain. Subsequently, Gunwar et al, (1990), *J Biol. Chem*, 265, 5466–5469 have published a second partial amino acid sequence of α3(IV) in which a serine was also found at position 15. Furthermore, an additional four amino acids were obtained by Hudson et al and these were the same as the amino acids predicted from the nucleotide sequence of clone pKEMC15.

pKEMC15 encodes all of the NC1 domain as well as 238 amino terminal residues of the collagenous repeat sequence Gly-Xaa-Yaa and 8 base pairs of the 3' untranslated region. Table 1 shows the amino-acid composition of NC1 α3(IV) derived from the sequence of pKEMC15 compared to that obtained from amino acid analysis of bovine M2* and human M28+++.

TABLE 1

Comparison of amino acid compositions of collagenase-resistant fragments from basement membrane with the composition of the bovine α3(IV) NC1 domain predicted from nucleotide sequence.

| Amino acid | Number of residues | | |
|---|---|---|---|
| | α3(IV) | M2* | M28+++ |
| Alanine | 20 | 18.5 | 19.2 |
| Phenylalanine | 15 | 14.1 | 16.9 |
| Lysine | 5 | 4.7 | 6.2 |
| Proline | 20 | 21.7 | 17.7 |
| Threonine | 15 | 14.7 | 19.3 |
| Cysteine | 12 | NE | NE |
| Glycine | 19 | 24.9 | 22.5 |
| Leucine | 15 | 17.1 | 18.2 |
| Glutamine/Glutamic acid | 19 | 21.3 | 20.6 |
| Valine | 8 | 9.2 | 10.4 |
| Asparagine/Aspartic acid | 14 | 14.2 | 14.5 |
| Histidine | 4 | 5.2 | 6.6 |
| Methionine | 9 | 7.3 | 3.0 |
| Arginine | 12 | 12.1 | 14.1 |
| Tryptophan | 4 | NE | NE |
| Isoleucine | 14 | 10.7 | 11.1 |
| Serine | 23 | 21.4 | 18.5 |
| Tyrosine | 7 | 6.9 | 6.2 |

Composition of M2* is from Butkowksi et al, (1985), J.Biol.Chem., 260, 8564–8570. Composition of M28+++ is from Butkowski et al (1980), J.Lab.Clin.Med.115, 365–373. NE: no amino acid determination made.

EXAMPLE 18

Comparative Sequence Analyses—The deduced amino acid sequence reveal s several features typical of type IV collagens. The NC1 domain is similar in length to α1(IV), α2(IV) and α5(IV) and contains 12 cysteine residues in identical places. Regions that are highly conserved between α1(IV), α2(IV) and α5(IV) are also highly conserved in α3(IV). The three imperfections in the Gly-Xaa-Yaa repeat sequence found in the 238 residues of the triple helical region abutting the NC1 domain in α3(IV) occur at identical points of the collagenous domain in human α1(IV), α2(IV) and α5(IV). Overall the sequqnce shows 71%, 60% and 70% amino acid identity with the NC1 domains of the human α1(IV), α2(IV) and α5(IV) chains.

It will be appreciated that the instant specification is set forth by way of illustration and not limitation, and that various modifications and changes may be made without departing from the spirit and scope of the present invention.

What is claimed:

1. An isolated recombinant polypeptide, which is a bovine α3 chain of type IV collagen, having the amino acid sequence of SEQ ID No 24, produced by the expression of the nucleic acid sequence of SEQ. ID No 1 in a transformed host cell.

2. An isolated recombinant polypeptide, which is a human α3 chain of type IV collagen, having the deduced amino acid sequence of SEQ ID No 25, produced by the expression of the nucleic acid sequence of SEQ. ID No 2 in a transformed host cell.

3. An isolated recombinant polypeptide having no more than 218 amino acids of the human α3 chain of type IV collagen (SEQ ID No. 25), containing the amino acid sequence: ISRCQVCMKKRH (SEQ ID No. 3), produced by the expression of the nucleic acid sequence of SEQ. ID No 2 in a transformed host cell.

* * * * *